US008926554B2

(12) United States Patent
Okuda et al.

(10) Patent No.: US 8,926,554 B2
(45) Date of Patent: Jan. 6, 2015

(54) MEDICINAL SOLUTION INJECTION DEVICE AND MEDICINAL SOLUTION INJECTION METHOD

(75) Inventors: Akinobu Okuda, Nara (JP); Tohru Nakamura, Osaka (JP); Soichiro Fujioka, Osaka (JP); Osamu Mizuno, Osaka (JP); Akihiro Ohta, Osaka (JP)

(73) Assignee: Panasonic Corporation, Osaka (JP)

( * ) Notice: Subject to any disclaimer, the term of this patent is extended or adjusted under 35 U.S.C. 154(b) by 482 days.

(21) Appl. No.: 13/394,906

(22) PCT Filed: Sep. 17, 2010

(86) PCT No.: PCT/JP2010/005691
§ 371 (c)(1),
(2), (4) Date: Mar. 8, 2012

(87) PCT Pub. No.: WO2011/033788
PCT Pub. Date: Mar. 24, 2011

(65) Prior Publication Data

US 2012/0197184 A1 Aug. 2, 2012

(30) Foreign Application Priority Data

Sep. 17, 2009 (JP) ................................ 2009-215339

(51) Int. Cl.
*A61M 31/00* (2006.01)
*A61J 1/20* (2006.01)
*A61J 1/22* (2006.01)

(52) U.S. Cl.
CPC . *A61J 1/2096* (2013.01); *A61J 1/22* (2013.01); *A61J 2200/76* (2013.01)
USPC ........................................................... 604/65

(58) Field of Classification Search
USPC ........................................................... 604/65
See application file for complete search history.

(56) References Cited

U.S. PATENT DOCUMENTS

2001/0018937 A1* 9/2001 Nemoto .......................... 141/27
2003/0036725 A1* 2/2003 Lavi et al. ...................... 604/91

FOREIGN PATENT DOCUMENTS

JP 59-139265 8/1984
JP 11-188095 7/1999
JP 11188095 A * 7/1999
JP 2000-189515 7/2000
JP 2004-329685 11/2004

OTHER PUBLICATIONS

International Search Report issued Nov. 2, 2010 in International (PCT) Application No. PCT/JP2010/005691, of which the present application is the national stage.

* cited by examiner

*Primary Examiner* — Jason Flick
(74) *Attorney, Agent, or Firm* — Wenderoth, Lind & Ponack, L.L.P.

(57) ABSTRACT

A medicinal solution injection apparatus 10 includes a composite needle 12 including a needle base portion 12*c*, an injection needle 12*d*, and an adjustment needle 12*e*, a pressure generating portion 13 configured to discharge a compressed air, a measuring portion 14 configured to measure a filling amount and a filling speed of a medicinal solution by measuring a position of a gasket 17*a* of a syringe 17, and a control portion 15 configured to control the pressure generating portion 13 and the measuring portion 14. The compressed air is introduced into a vial container 16 through an edge 12*h* of the adjustment needle 12*e* located above a liquid surface 16*a* of the medicinal solution in the vial container 16 (outside the liquid surface) to press the liquid surface 16*a* of the medicinal solution downward, so that a medicinal solution 16*b* is injected into the syringe 17 through an edge 12*i* of the injection needle 12*d* in the medicinal solution 16*b*. The medicinal solution injection apparatus 10 can accurately and efficiently inject the medicinal solution 16*b* of the vial container 16 into the syringe 17 while suppressing the medicinal solution 16*b* from foaming.

13 Claims, 16 Drawing Sheets

<CONTROL VIAL INTERNAL PRESSURE>

MEDICINAL SOLUTION INJECTION DEVICE AND MEDICINAL SOLUTION INJECTION METHOD

TECHNICAL FIELD

The present invention relates to a medicinal solution injection apparatus and a medicinal solution injection method used in a mixing operation for preparing a medicinal solution such as an injection solution in a syringe or the like in the field of medical care.

BACKGROUND ART

When a medicinal solution is administered to an admitted patient in a medical facility such as a hospital, the medicinal solution is often prepared by mixing different types of medicinal solutions obtained from different medicinal solution containers. Such a conventional mixing operation to prepare the medicinal solution often requires manpower of medical personnel such as nurses or pharmacists. An injection needle, for example, is manually inserted in the different medicinal solution containers to suction the medicinal solutions therefrom. This is a heavily time-consuming work for the medical personnel. Particularly when the medicinal solution is suctioned from a sealed medicinal solution container, for example, a sealed vial container, it is necessary to introduce air into the medicinal solution container during the suctioning of the medicinal solution therefrom (generally called pumping work) in order to adjust an internal pressure of the container. Thus, it imposes even a more time-consuming and complex work load on the medical personnel to suction the medicinal solution from the sealed container. Some of the medicinal solutions used in medical facilities need to be cautiously handled with a great care for safety. Under the circumstances described so far, there is a strong demand for a medicinal solution injection apparatus and a medicinal solution injection method that enable safe handling of any medicinal solutions with less work load.

FIG. 16 is a structural view of the medicinal solution injection apparatus disclosed in the Patent Literature 1. The medicinal solution injection apparatus illustrated in FIG. 16 is configured to inject a solution 4 from any of a plurality of liquid bottles 3 into a medicinal agent bottle 1 to dissolve a powdery or particulate medicinal agent 2 in the medicinal agent bottle 1. As illustrated in FIG. 16, a compressed gas feeder 5 feeds a compressed gas into a space above the solution 4 in the liquid bottle 3 through an injection needle 7 by using a feed pipe 6 to thereby press the solution 4 at an adequately higher pressure than atmospheric pressure, so that the solution 4 is injected into the medicinal agent bottle 1 through a feed pipe 8. There are provided opening/closing cocks 9 between the injection needles 7 of the liquid bottles 3 and the feed pipes 6, and also between the injection needle 7 of the medicinal agent bottle 1 and the feed pipe 8. The opening/closing cocks 9 are usually kept closed, but any of the opening/closing cocks 9 that needs to be used is opened among the opening/closing cock 9 of the liquid bottle 3. In the illustration of FIG. 16, the opening/closing cock 9 of the liquid bottle 3 on the right side and the opening/closing cock 9 of the medicinal agent bottle 1 alone are opened, and the solution 4 is currently injected into the medicinal agent bottle 1. The apparatus according to the Patent Literature 1 is designed to safely inject the solution 4 into the medicinal agent bottle 1 semi-automatically by using the compressed gas while using no manpower.

CITATION LIST

Patent Literature

PATENT LITERATURE 1: Japanese Unexamined Patent Application Publication No. 59-139265

SUMMARY OF THE INVENTION

Technical Problem

The medicinal solution injection apparatus illustrated in FIG. 16 is designed to blow the compressed gas through the injection needle 7 down to the liquid surface of the solution 4. In the case where the edge of the injection needle 7 is too close to the liquid surface of the solution 4, the solution 4 (medicinal solution) is entrained in the incoming compressed gas and thereby becomes foamy. To prevent this problem from happening, it is necessary to adjust how far the injection needle 7 should be inserted and an inflow of the compressed gas. Reducing the inflow of the compressed gas to prevent the solution 4 from foaming, it takes more time to inject the solution 4, making the operation less efficient.

In the medicinal solution injection apparatus illustrated in FIG. 16, the liquid bottles 3 (medicinal solution containers) where the solution 4 (medicinal solution) is contained always have positive internal pressures because of the pressure of the compressed gas supplied thereto. This generates the risk that the solution 4 blows out when the opening/closing cock 9 of the medicinal solution bottle 1 is opened.

To solve the conventional technical problems, the present invention provides a medicinal solution injection apparatus and a medicinal solution injection method capable of accurately and efficiently injecting a medicinal solution contained in a medicinal solution container into a syringe while preventing the medicinal solution from foaming.

Solution to Problem

To achieve the object, the present invention provides a medicinal solution injection apparatus, including: a composite needle including a receiving port for receiving a medicinal solution container, a holding port for holding a syringe, an injection needle inserted through a needle base portion to communicate the receiving port with the holding port, and an adjustment needle inserted through the needle base portion from a side surface of the needle base portion to the receiving port and located in parallel with the injection needle in the receiving port; a fluid feeding portion configured to feed a fluid into the medicinal solution container received by the receiving port through a feed tube connected to an end portion of the adjustment needle on a side of the side surface; a measuring portion configured to measure at least one of a filling amount and a filling speed of a medicinal solution injected into the syringe from the medicinal solution container by the fluid fed from the fluid feeding portion through the injection needle based on a position of a gasket in the syringe held by the holding port; and a control portion configured to control a feeding amount of the fluid from the fluid feeding portion based on a result of the measurement by the measuring portion.

The present invention further provides a medicinal solution injection method comprising steps of: preparing a medicinal solution injection apparatus comprising a composite needle including a needle base portion, an injection needle inserted through the needle base portion to communicate a receiving port with a holding port, and an adjustment needle inserted through the needle base portion from a side surface of the needle base portion to the receiving port and located in parallel with the injection needle in the receiving port; holding a syringe in the holding port; receiving a medicinal solution container in the receiving port; locating an edge of the adjustment needle above a liquid surface of a medicinal solution contained in the medicinal solution container after the injection needle and the adjustment needle are inserted in the medicinal solution container; measuring a front-end position of a gasket of the syringe; feeding a fluid into the medicinal solution container through an end portion of the adjustment needle on a side of the side surface using the fluid feeding portion based on the front-end position of the gasket; and injecting the medicinal solution contained in the medicinal solution container into the syringe through the injection needle.

Effect of the Invention

The medicinal solution injection apparatus and the medicinal solution injection method provided by the present invention can accurately and efficiently inject the medicinal solution contained in the medicinal solution container into the syringe while preventing the medicinal solution from foaming.

DESCRIPTION OF EMBODIMENTS

Figure 1A:
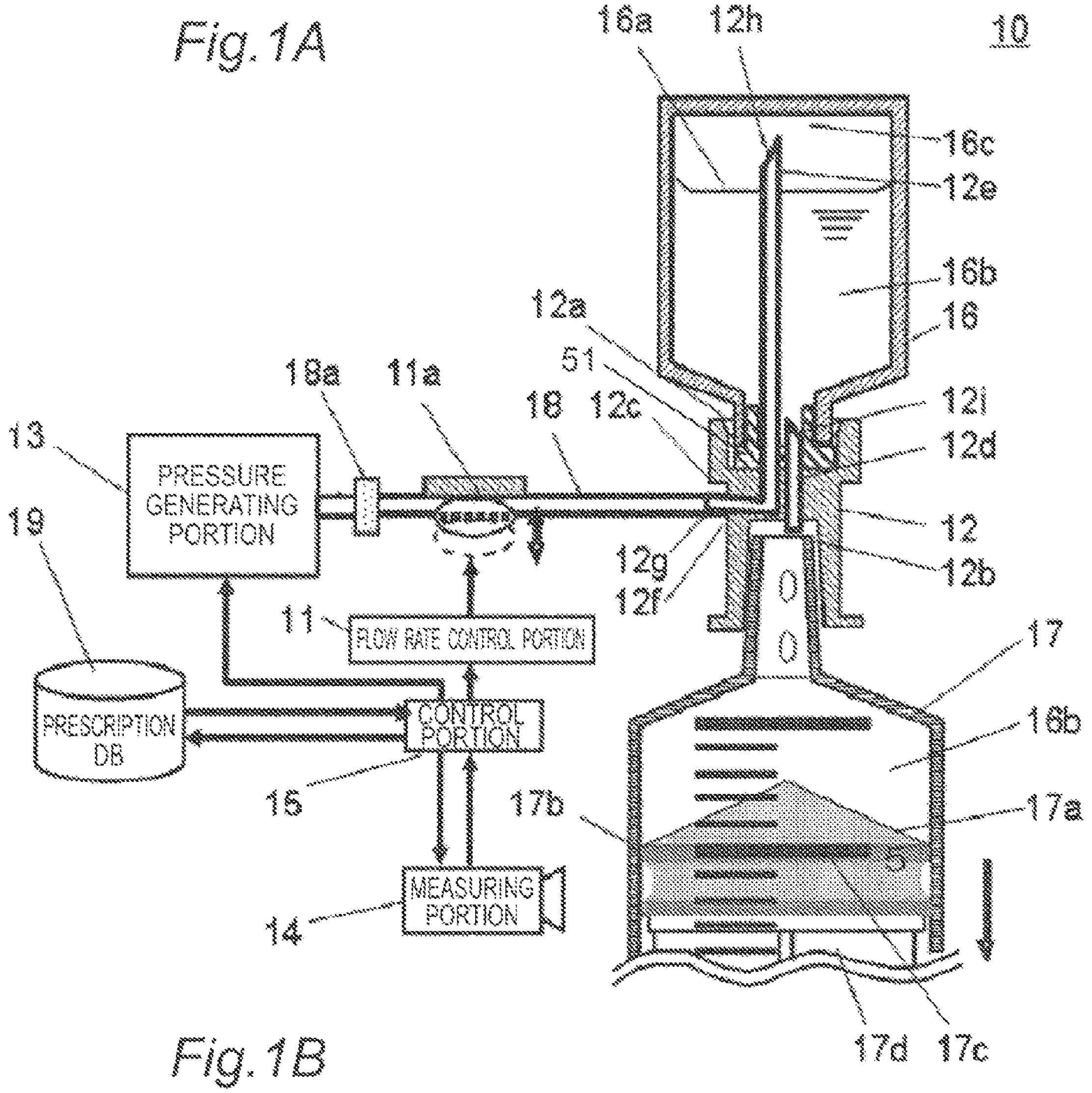
FIG. 1A is a side view schematically illustrating an overall structure of a medicinal solution injection apparatus according to an embodiment 1 of the present invention.

Hereinafter, embodiments of the present invention are described referring to the accompanied drawings. The same structural elements are simply illustrated with the same reference numerals so that redundant description may be omitted. For ease of understanding of structural characteristics, the drawings per se are schematically illustrated so that structural elements are clearly grasped.

Embodiment 1

Figure 1B:
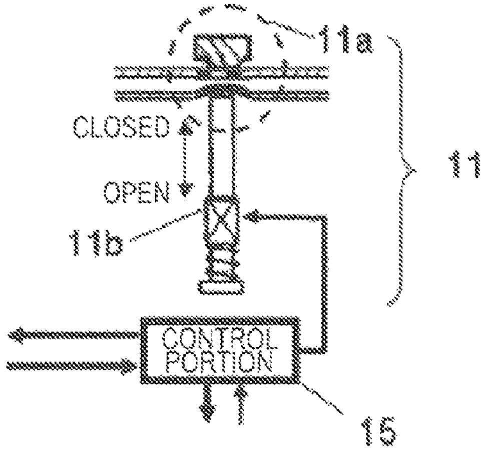
FIG. 1B is an enlarged view of a flow rate control portion.

FIGS. 1A and 1B are schematic illustrations of a medicinal solution injection apparatus 10 according to an embodiment 1 of the present invention. FIG. 1A is a side view schematically illustrating an overall structure of the medicinal solution injection apparatus 10. FIG. 1B is an enlarged view of a flow rate control portion 11.

As illustrated in FIGS. 1A and 1B, the medicinal solution injection apparatus 10 according to the embodiment 1 is provided with a composite needle 12 for injecting a medicinal solution, a pressure generating portion 13 configured to discharge a compressed gas, a flow rate control portion 11 configured to control a flow rate of the compressed gas, a measuring portion 14 configured to measure a filling amount and a filling speed of the medicinal solution, and a control portion 15. The control portion 15 controls the pressure generating portion 13, flow rate control portion 11, and measuring portion 14.

The composite needle 12 has a needle base portion 12*c*, an injection needle 12*d*, and an adjustment needle 12*e*. The needle base portion 12*c* is made of an elastic material such as a resin. An upper section of the needle base portion 12*c* is dented so that a receiving port 12*e* for receiving a vial container 16 (medicinal solution container) is formed. A lower section of the needle base portion 12*c* is dented so that a holding port 12*b* for holding a syringe 17 is formed. The injection needle 12*d* penetrates through the needle base portion 12*c* from the receiving port 12*a* to the holding port 12*b*. The adjustment needle 12*e* penetrates through the needle base portion 12*c* from a side surface 12*f* of the needle base portion 12*c* to the receiving port 12*a* as far as above the receiving port 12*a* in parallel with the injection needle 12*d*.

When an opening side of the vial container 16 sealed with a rubber cap 51 is seated in the receiving port 12*a*, a wall surface of the receiving port 12*a* closely contacts the opening side of the vial container 16 and the rubber cap 51, so that the vial container 16 is kept hermetically sealed except paths passing through the injection needle 12*d* and the adjustment needle 12*e*. When an injection-port side of the syringe 17 is seated in the holding port 12*b*, a wall surface of the holding port 12*b* closely contacts the injection-port side of the syringe 17, so that the syringe 17 is kept hermetically sealed except a path passing through the injection needle 12*d*.

The pressure generating portion (fluid feeding portion) 13 discharges compressed air, which is an example of the compressed gas, into the vial container 16 through a tube (feed tube) 18 connected to an end portion 12*g* of the adjustment needle 12*e* constituting the composite needle 12. The measuring portion 14 measures a front-end position 17*b* of a gasket 17*a* in the syringe 17 held by the holding port 12*b* of the composite needle 12 to thereby measure the filling amount and the filling speed of the medicinal solution injected into the syringe 17.

An edge 12*h* of the adjustment needle 12*e* is disposed above a liquid surface 16*a* of the vial container 16 (outside the liquid surface) to introduce the compressed air into the vial container 16 through the edge 12*h* of the adjustment needle 12*e*. The compressed air introduced into the vial container 16 presses the liquid surface 16*a* of the medicinal solution downward. As a result, a medicinal solution 16*b* in the vial container 16 is injected into the syringe 17 through the injection needle 12*d* having an edge 12*i* placed in the medicinal solution 16*b*.

Next, a basic operation of the medicinal solution injection apparatus 10 according to the embodiment 1 is described.

The compressed air generated and discharged by the pressure generating portion 13 illustrated in FIG. 1A travels through the tube 18, and then introduced into the vial container 16 toward a bottom section 16*c* thereof through the edge 12*h* of the adjustment needle 12*e* of the composite needle 12 to press the liquid surface 16*a* of the medicinal solution. Because the edge 12*h* of the adjustment needle 12*e* projects upward from the liquid surface 16*a* of the medicinal solution, the compressed air is not directed toward the liquid surface 16*a* of the medicinal solution but is directed upward toward the bottom section 16*c* of the vial container 16. The compressed air thus introduced into the vial container 16 does not catch up the medicinal solution 16*b*. This eliminates the risk of foaming the medicinal solution 16*b*.

When the liquid surface 16*a* of the upper portion of the medicinal solution 16*b* is pressed downward by the compressed air, the medicinal solution 16*b* is guided into the injection needle 12*d* placed in the lower portion of the medicinal solution and then injected into the syringe 17 therethrough. Apart of the medicinal solution 16*b* thus injected pushes the gasket 17*a* in the syringe 17 downward.

The measuring portion 14 reads the front-end position 17*b* of the gasket 17*a* in the syringe 17 by checking a scale mark 17*c* of the syringe 17 to thereby measure the filling amount of the medicinal solution injected into the syringe 17. For example, the measuring portion 14 may be equipped with a camera used for measurement where an entire travelling stroke of the gasket 17*a* is included in an imaging visual field, wherein images of the gasket 17*a* and the scale mark 17*c* captured by the measurement camera are image-processed, so that the scale mark 17*c* at the front-end position 17*b* of the gasket 17*a* is recognized. The measuring portion 14 measures the filling amount of the medicinal solution using a result of the image recognition. The filling amount (measured value) of the medicinal solution measured by the measuring portion 14 is converted into, for example, an electrical signal and then transmitted to the control portion 15 to be compared to a predefined amount of the medicinal solution to be injected.

In the case where the filling amount of the medicinal solution in the syringe 17 measured by the measuring portion 14 has not yet reached the predefined amount of the medicinal solution, the control portion 15 continues to press the liquid surface 16*a* downward by continuously feeding the compressed air from the pressure generating portion 13 so that the medicinal solution 16*b* is further injected into the syringe 17. When the filling amount of the medicinal solution in the syringe 17 measured by the measuring portion 14 reaches the predefined amount of the medicinal solution, the control portion 15 ceases to feed the compressed air from the pressure generating portion 13 to terminate the injection of the medicinal solution 16*b* into the syringe 17. Information of prescriptions, for example, predefined amounts of medicinal solutions and different types of medicinal solutions, is provided from a prescription database (hereinafter, called "prescription DB") 19 according to the needs of treatments for patients. In the prescription information stored in the prescription DB 19, operation details when the medicinal solution 16*b* is injected into the syringe 17 are recorded.

As a result of the operation described so far, the medicinal solution injection apparatus 10 can accurately and efficiently inject the medicinal solution 16*b* of the vial container 16 into the syringe 17 while preventing the medicinal solution 16*b* from foaming. Moreover, the medicinal solution injection apparatus 10 can arrange the vial container 16 and the syringe 17 at the upper and lower sections of the needle base portion 12*c*. The measuring portion 14 directly reads the front-end position 17*b* of the gasket 17*a* by checking the scale mark 17*c* of the syringe 17. Accordingly, a compact apparatus, which is convenient for space saving, can be achieved.

In place of measuring the front-end position 17*b* of the gasket 17*a*, the measuring portion 14 may measure a rear-end position of a plunger 17*d* of the syringe 17 (not illustrated in the drawings) to read the filling amount of the medicinal solution 16*b*. The measuring portion 14 may directly measure the rear-end position of the plunger 17*d* by using, for example, a linear potentiometer. Thus, the measuring portion 14 does not need to image-process the images captured by the measurement camera, thereby more accurately reading the filling amount of the medicinal solution 16*b* and more reliably controlling the filling of the medicinal solution 16*b*.

The measuring portion 14 may measure and output the filling speed of the medicinal solution injected into the syringe 17 to the control portion 15 in addition to or in place of the filling amount of the medicinal solution injected into the syringe 17. In this case, the measuring portion 14 measures the filling amount by different timings in the syringe 17, and calculates the filling speed by arithmetically operating the measured filling amounts.

In place of placing the syringe 17 in the holding port 12*b* in the lower section of the needle base portion 12*c*, a graduated cylinder (not illustrated in the drawings) may be placed in the holding port 12*b* to inject the medicinal solution 16*b* into the graduated cylinder. In this case, the measuring portion 14 detects the liquid surface of the medicinal solution 16*b* filled into the graduated cylinder and outputs a feedback detection result to the control portion 15 to control the amount of the medicinal solution 16*b* to be injected.

Referring to FIG. 1B, the flow rate control portion 11 changes an inner-diameter sectional area of the tube 18 by pushing a part of the tube 18 to change the flow rate of the compressed air. The flow rate control portion 11 includes a flow rate control valve 11*a*. The flow rate control portion 11 is configured to continuously adjust the flow rate of the compressed air by opening and closing the flow rate control valve 11*a*. As illustrated in FIG. 1B, the flow rate control valve 11*a* is opened and closed by a valve driver 11*b* in which an electronic solenoid is used. Using the function of the valve driver 11*b*, the control portion 15 can control the flow rate control portion 11 depending on the filling amount or the filling speed of the medicinal solution 16*b* measured by the measuring portion 14 to thereby change the inflow of the compressed air. This structural feature can slow down the filling speed of the medicinal solution 16*b* when the filling amount of the medicinal solution 16*b* approaches an ultimate target value, thereby injecting an exact amount of the medicinal solution into the syringe 17. With this configuration, the medicinal solution can be injected under any conditions that satisfy physical properties of the medicinal solution 16*b* (for example, viscosity).

A bacteria blocking filter 18*a* may be provided between the pressure generating portion 13 and the flow rate control portion 11. With this configuration, bacteria included in the compressed air is prevented from entering the vial container 16 through the tube 18, so that possible contamination of the medicinal solution 16*b* with bacteria can be avoided when the medicinal solution 16*b* is injected from the vial container 16 into the syringe 17.

The control portion 15 may be configured to inject the medicinal solution 16*b* of the vial container 16 into the syringe 17 based on data of the prescription DB 19 (for example, information of prescriptions and medications). With this configuration, the medicinal solution 16*b* can be accurately injected into the syringe 17 based on data of treatments for patients and types of the medicinal solution 16*b*.

Figure 2:
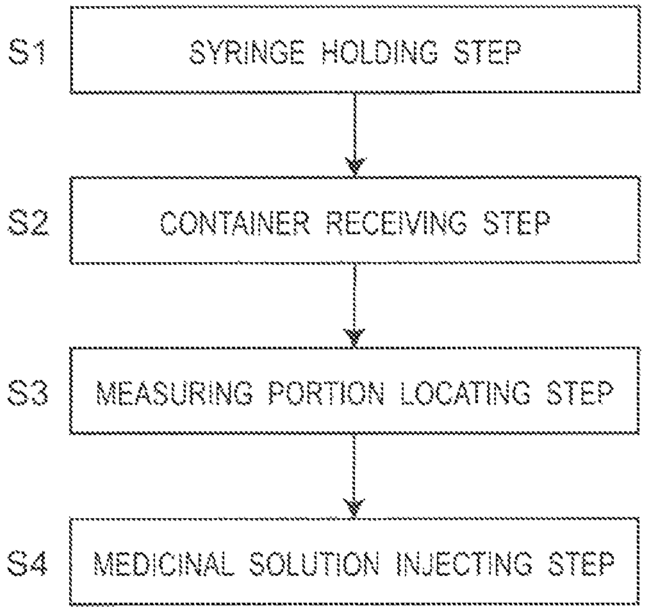
FIG. 2 is a flow chart of a medicinal solution injection method according to the embodiment 1.
Figure 3:
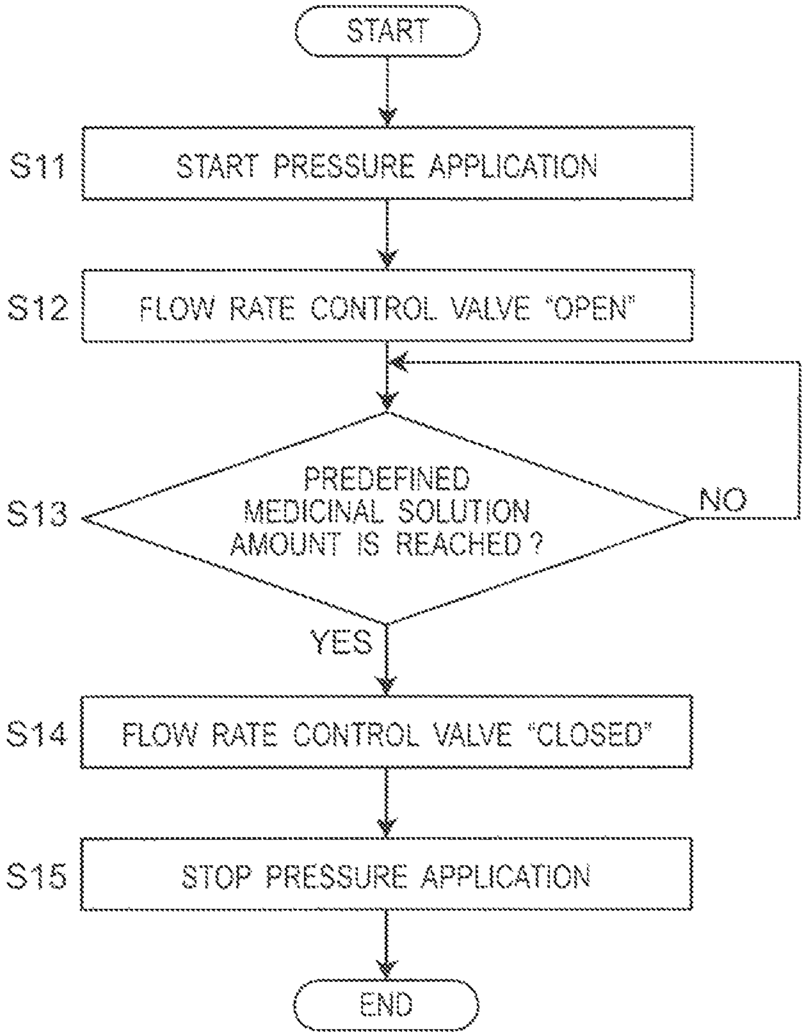
FIG. 3 is a flowchart illustrating in detail a medicinal solution injecting step of the medicinal solution injection method according to the embodiment 1.

A medicinal solution injection method using the medicinal solution injection apparatus 10 according to the embodiment 1 is hereinafter described. FIG. 2 is a flowchart of a medicinal solution injection method according to the embodiment 1. FIG. 3 is a flow chart specifically illustrating a medicinal solution injecting step S4 illustrated in the medicinal solution injection method of FIG. 2 according to the embodiment 1.

As illustrated in FIG. 2, the medicinal solution injection method according to the embodiment 1 uses the medicinal solution injection apparatus 10 described so far (see FIG. 1). The medicinal solution injection method includes a syringe holding step S1, a container receiving step S2, a measuring portion locating step S3, and a medicinal solution injecting step S4.

The syringe holding step S1 is a step in which the syringe 17 is held by the holding port 12*b* formed in the needle base portion 12*c* of the composite 12. The gasket 17*a* of the syringe 17 is pushed upward to an upper section of the syringe 17 so that any extra air is not introduced into the syringe 17.

The container receiving step S2 is a step in which the vial container 16 turned upside down is received by the receiving port 12*a* of the needle base portion 12*c*, the edge 12*i* of the injection needle 12*d* and the edge 12*h* of the adjustment needle 12*e* are let through the rubber cap 51 to be inserted into the vial container 16, and the edge 12*h* of the adjustment needle 12*e* is then located above the liquid surface 16*a* of the medicinal solution in the vial container 16 (outside the liquid surface). When the edge 12*h* of the adjustment needle 12*e* is thus located above the liquid surface 16*a* of the medicinal solution, possible foaming of the medicinal solution 16*b* is avoided when the compressed air is introduced from the pressure generating portion 13 into the vial container 16. Accordingly, the medicinal solution 16*b* can be accurately and efficiently injected into the syringe 17.

The measuring portion locating step S3 locates an imaging device of the measuring portion 14, for example, a measurement camera. The measurement camera is located so that the front-end position 17*b* of the gasket 17*a* in the syringe 17 can be read by referring to the scale mark 17*c* of the syringe 17.

Then, the medicinal solution injecting step S4 feeds the compressed air from the pressure generating portion 13 into the vial container 16 through the edge 12*h* of the adjustment needle 12*e* to inject the medicinal solution 16*b* of the vial container 16 into the syringe 17 through the injection needle 12*d*.

The method thus performed can accurately and efficiently inject the medicinal solution 16*b* of the vial container 16 into the syringe 17 without foaming the medicinal solution 16*b*.

The medicinal solution injecting step S4 is further described referring to FIG. 3.

In the flow chart of FIG. 3 illustrating the medical solution injecting step, firstly, the pressure generating portion 13 starts to apply a pressure in order to feed the compressed air into a space above the liquid surface 16*a* of the medicinal solution in the vial container 16 through the tube 18 and the adjustment needle 12*e* (step S11).

Next, the flow rate control valve 11*a* on the downstream side of the pressure generating portion 13 is opened, and the compressed air introduced from the pressure generating portion 13 into the vial container 16 through the tube 18 and the adjustment needle 12*e* starts to press the liquid surface 16*a* of the medicinal solution downward (step S12).

As the liquid surface 16*a* of the medicinal solution is thus pressed, the medicinal solution 16*b* is accordingly injected into the syringe 17 held by the holding port 12*b* of the composite needle 12. The injection of the medicinal solution 16*b* continues until a medicinal solution amount predefined in a prescription from the prescription DB 19 is reached (step S13).

The flow rate control valve 11*a* is closed when the amount of the injected medicinal solution 16*b* reaches the predefined medicinal solution amount (step S14). The feed of the compressed air by the pressure generating portion 13 stops to end the pressure application (step S15).

The method thus performed can accurately and efficiently inject the medicinal solution 16*b* of the vial container 16 into the syringe 17 while suppressing the medicinal solution 16*b* from foaming.

Another medicinal solution injection method using the medicinal solution injection apparatus 10 according to the embodiment 1 is hereinafter described.

Figure 4:
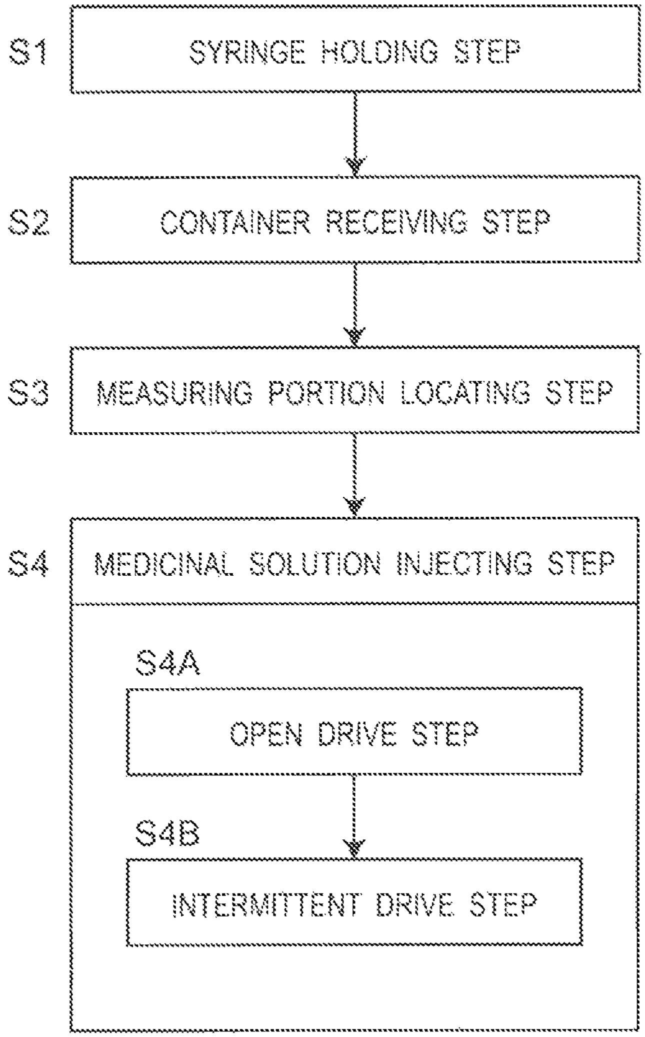
FIG. 4 is a flow chart of another medicinal solution injection method according to the embodiment 1.
Figure 5:
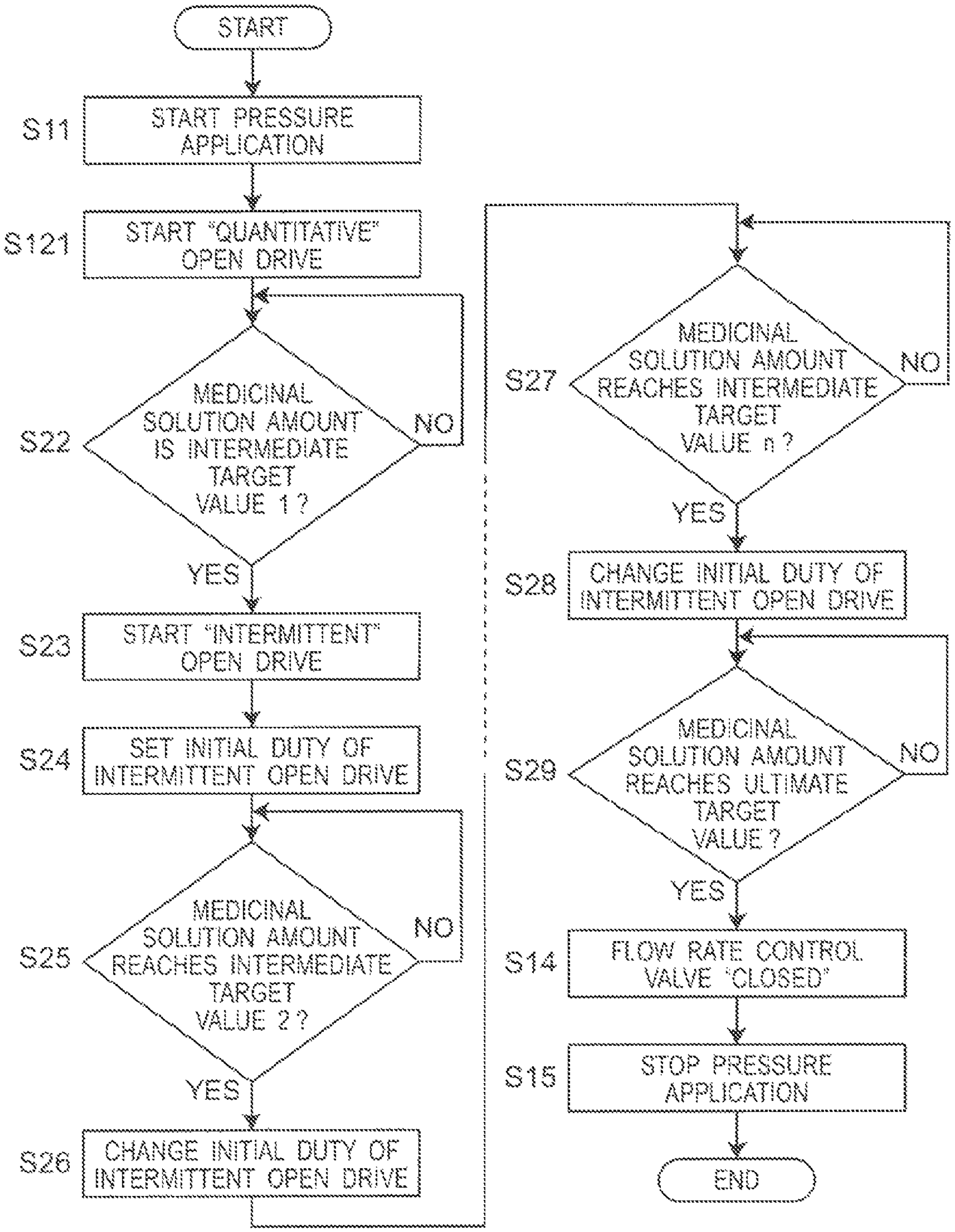
FIG. 5 is a flowchart illustrating in detail a medicinal solution injecting step of the other medicinal solution injection method according to the embodiment 1.

FIG. 4 is a flow chart of another medicinal solution injection method according to the embodiment 1. FIG. 5 is a flow chart specifically illustrating a medicinal solution injecting step S4 in the another medicinal solution injection method of FIG. 4 according to the embodiment 1.

As illustrated in FIG. 4, the another medicinal solution injection method according to the embodiment 1 uses the medicinal solution injection apparatus 10 (see FIG. 1). The another medicinal solution injection method includes a syringe holding step S1, a container receiving step S2, a measuring portion locating step S3, and a medicinal solution injecting step S4. In the medicinal solution injection method of FIG. 4, the syringe holding step S1, container receiving step S2, and measuring portion locating step S3 are similar to the steps of the method illustrated in FIG. 2. The medicinal solution injecting step S4 including an open drive step S4A and an intermittent drive step S4B is different to the medicinal solution injection method illustrated in FIG. 2. The open drive step S4A is a step in which the flow rate control valve 11*a* of the flow rate control portion 11 is left open to send the compressed air from the pressure generating portion 13. The intermittent drive step S4B is a step in which the flow rate control valve 11*a* is repeatedly opened and closed during the operation. During the intermittent drive step S4B, a length of time when the flow rate control valve 11*a* is left close is gradually increased in accordance with an increase of the amount of the medicinal solution filling the syringe 17 so that the inflow of the compressed air is gradually decreased.

According to the method, as the amount of the medicinal solution filling the syringe 17 is approaching the ultimate target value, the inflow of the compressed air is gradually decreased. This effectively prevents such an accident that the medicinal solution 16*b* is overly injected into the syringe 17. As a result, this method realizes an accurate and efficient injection of the medicinal solution 16*b* into the syringe 17.

Figure 6A:
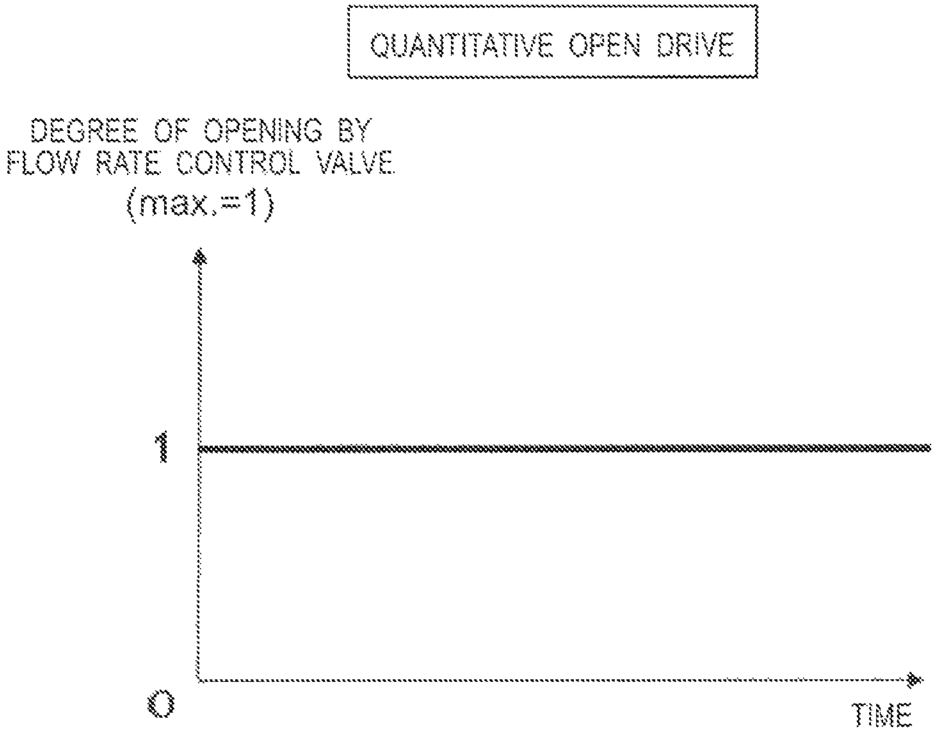
FIG. 6A is a diagram illustrating a drive pattern of a flow rate control valve according to the embodiment 1 on a time shaft (during quantitative open drive).
Figure 6B:
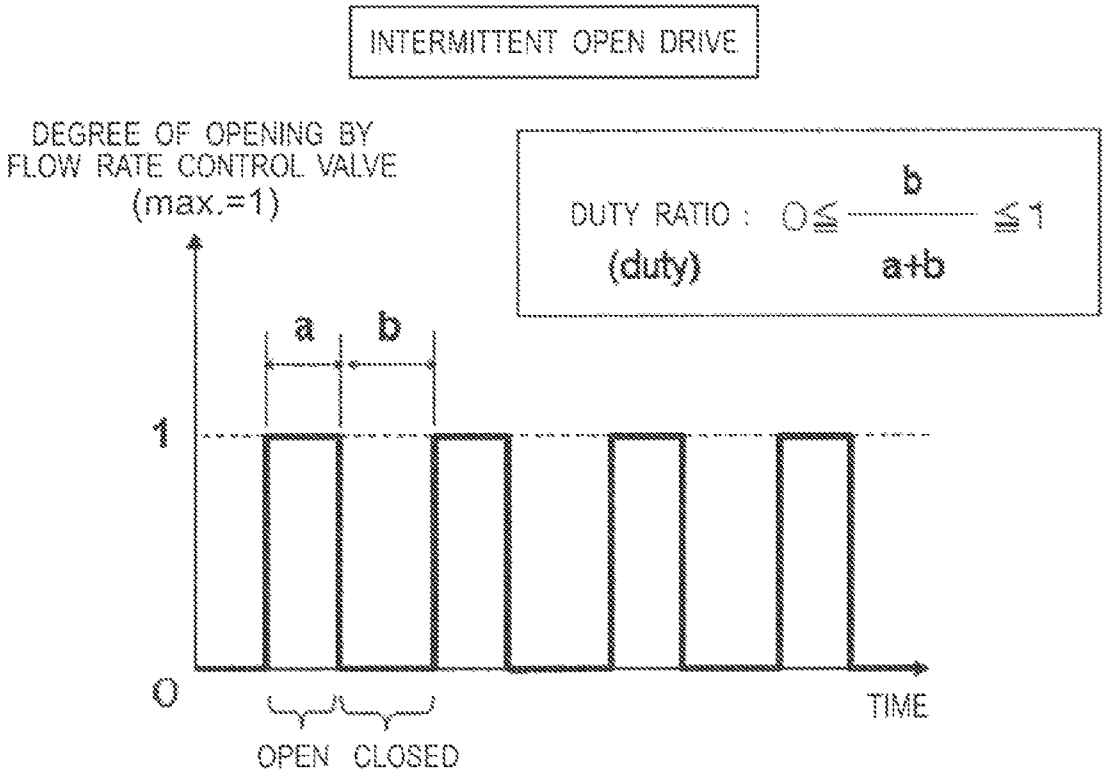
FIG. 6B is a diagram illustrating a drive pattern of the flow rate control valve according to the embodiment 1 on the time shaft (during intermittent open drive).

The medicinal solution injecting step S4 illustrated in FIG. 4 is described in further detail referring to FIGS. 5, 6A and 6B. Steps S21 and S22 in the flow chart of FIG. 5 are comparable to the open drive step S4 of FIG. 4, and Steps S23 to S29 in the flow chart are comparable to the intermittent drive step S4B of FIG. 4. FIGS. 6A and 6B are diagrams illustrating drive patterns of a degree of opening of the flow rate control valve 11*a* according to the embodiment 1 on a time shaft. FIG. 6A illustrates a drive pattern during the quantitative open drive, and FIG. 6B illustrates a drive pattern during the intermittent open drive.

Referring to the flow chart of FIG. 5 illustrating the medicinal solution injection to prevent the excess injection, the pressure generating portion 13 starts to apply a pressure through the tube 18 and the adjustment needle 12*e* immediately after the injection flow starts in order to send the compressed air into the space above the liquid surface 16*a* of the medicinal solution in the vial container 16 (step S11). Near the ending of the injection flow, when the amount of the injected medicinal solution 16*b* reaches the predefined medicinal solution amount or the ultimate target value, the flow rate control valve 11*a* becomes a closed state (step S14). The pressure generating portion 13 ceases to send the compressed air so that the pressure application ends (step S15). As described so far, Step S11 immediately after the injection flow starts and Steps S14 and S15 near the ending of the injection flow are the same steps as those illustrated in the flow chart of FIG. 3 illustrating the medicinal solution injection.

When simply controlling the steps to start and end the medicinal solution injection as illustrated in FIG. 3, the flow rate control valve 11*a* does not become a closed state but is kept open until injecting the medical solution 16*b* by only the predefined medicinal solution amount. Therefore, the medicinal solution 16*b* exceeding the predefined medicinal solution amount is possibly injected in the case where the injection of the medicinal solution 16*b* is comparatively accelerated in order to finish the injection in less time. Slowly injecting the medicinal solution 16*b* over a long period of time to prevent such an accident that the medicinal solution is overly injected, for example, the medicinal solution injecting step S4 results in a poor work efficiency.

To prevent the medicinal solution from being overly injected, the medicinal solution injecting step S4 includes the open drive step S4A and the intermittent drive step S4B. Specifically describing these steps, in the flow chart of the medicinal solution injection illustrated in FIG. 5, the quantitative open drive is started after the pressure application is started (step S11) (step S21).

As illustrated in FIG. 6A, the quantitative open drive sets the degree of opening of the flow rate control valve 11*a* to 1 (fully opens the flow rate control valve 11*a*) to lead the compressed air into the vial container 16. The degree of opening of the flow rate control valve 11*a* is expressed in a predefined numeral range from 0 to 1. When the degree of opening is 1, the flow rate control valve 11*a* becomes a fully opened state. When the degree of opening is 0, the flow rate control valve 11*a* becomes a fully closed state.

When the amount of the medicinal solution in the syringe 17 reaches an intermediate target value 1 during the ongoing quantitative open drive (step S22), the quantitative open drive is ceased to start the intermittent open drive (step S23). As illustrated in FIG. 6B, the intermittent open drive is a drive method in which an opening time "a" when the degree of opening of the flow rate control valve 11*a* is set to 1 (fully opens the flow rate control valve 11*a*) and a closing time "b" when the degree of opening is set to 0 (fully closes the flow rate control valve 11*a*) are alternately repeated during the operation. The intermittent open drive can easily adjust the amount of the compressed air flowing from the pressure generating portion 13 into the vial container 16 by stepwisely changing a ratio between the opening time "a" and the closing time "b" due to opening and closing the flow rate control valve 11*a*. When a duty ratio between the opening time "a" and the closing time "b" is periodically changed, the inflow of the compressed air per unit time can be changed. As a result, the filling speed of the medicinal solution 16*b* injected into the syringe 17 can be adjusted.

In the description given below, a proportion of the closing time "b" (off duty ratio) is used as the duty ratio between the opening time "a" and the closing time "b". The duty ratio thus set is defined by the following formula.

$$0 \leq \frac{b}{a+b} \leq 1 \qquad \text{[FORMULA 1]}$$

a: opening time
b: closing time

When the intermittent open drive starts (step S23), the duty ratio in an initial stage of the intermittent open drive is set to a relatively low value, for example, 0.5 (a=b=0.5) (step S24). The intermittent open drive starts with the duty ratio of 0.5 and continues until the medicinal solution amount reaches an intermediate target value 2 (step S25). The duty ratio (off duty ratio) of the intermittent open drive is changed when the amount of the medicinal solution amount reaches the intermediate target value 2 (step S26). Because the medicinal solution amount approaches the ultimate target value at the time that the intermediate target value, the duty ratio (off duty ratio) is updated to a value larger than the initial duty ratio, for example, 0.6 (a=0.4, b=0.6). This decreases the compressed air flowing into the vial container 16 per unit time, thereby slowing down the filling speed of the medicinal solution 16*b*.

Every time when the medicinal solution amount reaches an intermediate target value "n" (step S27) by repeating the intermittent open drive, the duty ratio of the intermittent open drive (off duty ratio) is updated to slightly larger values, for example, 0.7, 0.8, 0.85, 0.9, . . . and so on (step S28). The operation described so far continues until the medicinal solution amount reaches the ultimate target value (step S29). When it is determined that the medicinal solution amount reaches the ultimate target value, the flow rate control valve 11*a* becomes a closed state with the degree of opening being 0. Then, the operation of the pressure generating portion 13 is stopped to end the pressure application (step S15).

As the medicinal solution amount is getting closer to the ultimate target value, the duty ratio of the intermittent open drive (off duty ratio) is stepwisely increased. Then, the flow rate control valve 11*a* comes closer to a substantially closed state, and the filling speed of the medicinal solution 16*b* gradually slows down. Accordingly, a residual pressure of the compressed air remaining in the vial container 16 after the flow rate control valve 11*a* is fully closed prevents the medicinal solution 16*b* from overly flowing into the syringe 17.

Figure 7:
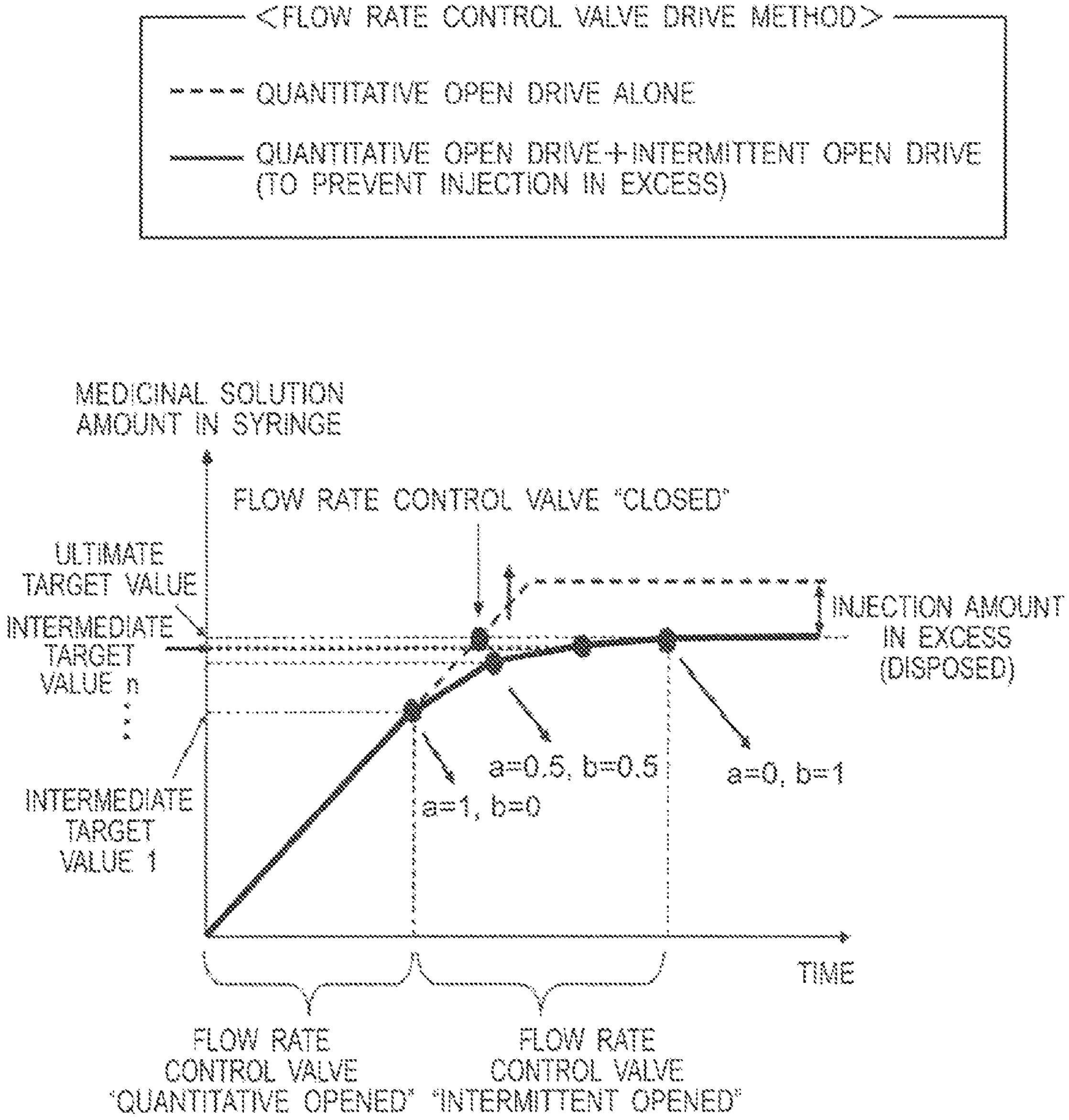
FIG. 7 is a diagram illustrating a variation of a medicinal solution amount with time when an ultimate target value of the medical solution is injected by the medicinal solution injection method including an intermittent drive step according to the embodiment 1.

FIG. 7 is a diagram illustrating a variation of the medicinal solution amount with time when injecting the medicinal solution amount of the ultimate target value into the syringe 17 by the medical solution injection method including the intermittent drive step according to the embodiment 1. As illustrated in FIG. 7, in the open drive step S4A, the flow rate control valve 11*a* is driven in the quantitative opened state until the medicinal solution amount originally 0 reaches the intermediate target value 1. Then, the medicinal solution amount can reach the intermediate target value 1 in a shortest period of time. In the intermittent drive step S4B, the flow rate control valve 11*a* is driven in the intermittent opened state until the medicinal solution amount having reached the intermediate target value 1 finally reaches the ultimate target value. That is, the valve is driven in the intermittent opened state with the duty ratio (off duty ratio) being gradually increased. Accordingly, the inflow of the compressed air and the filling speed of the medicinal solution 16*b* both drop by the time when the ultimate target value is reached. Therefore, the medicinal solution 16*b*, which is prevented from overly flowing into the syringe 17 by the residual pressure of the compressed air, can be injected into the syringe 17 with high accuracy. Because the medicinal solution 16*b* is injected in a shortest period of time until the intermediate target value 1 is reached, the medicinal solution 16*b* can be accurately and efficiently injected efficiently. As illustrated with a broken line in FIG. 7, in the case where the flow rate control valve 11*a* is left open by the open drive step S4A alone before the ultimate target value is reached, the residual pressure in the vial container 16 causes an excessive inflow. This case is inefficient since it is necessary to remove the medicinal solution 16*b* in excess later. The medicinal solution injection method according to the embodiment 1 can avoid such an inefficient operation that requires the disposal of the medicinal solution 16*b*.

To perform the medicinal solution injection method described so far, the flow rate control portion 11 of the medicinal solution injection apparatus 10 illustrated in FIG. 1 is provided with the flow rate control valve 11*a* which sets the degree of opening in the inner diameter of the tube 18 to 0 or 1. The flow rate control valve 11*a* is controlled so that the degree of opening is periodically set to 0 or 1 based on the predefined duty ratio. With this configuration, changing the degree of opening with time while maintaining a certain pressure level of gas such as compressed air, the medicinal solution 16*b* can be efficiently and speedily filled into the syringe 17, or the medicinal solution 16*b* in an exact amount can be filled into the syringe 17.

The flow rate control valve 11*a* is controlled to set the degree of opening to 1 until the filling amount of the medicinal solution 16*b* in the syringe 17 reaches the predefined filing amount. After the predefined filling amount is reached, the closing time when the degree of opening is 0 is inserted during the medicinal solution injection at regular intervals. At this time, the closing time is gradually extended by the time when the filling amount of the medicinal solution having reached the predefined filling amount reaches the ultimate filling amount. Accordingly, the medicinal solution 16*b* can be efficiently filled into the syringe 17, and the amount of the medicinal solution 16*b* can be accurately filled. Further, the excess injection of the medicinal solution 16*b* can be prevented.

Embodiment 2

Figure 8:
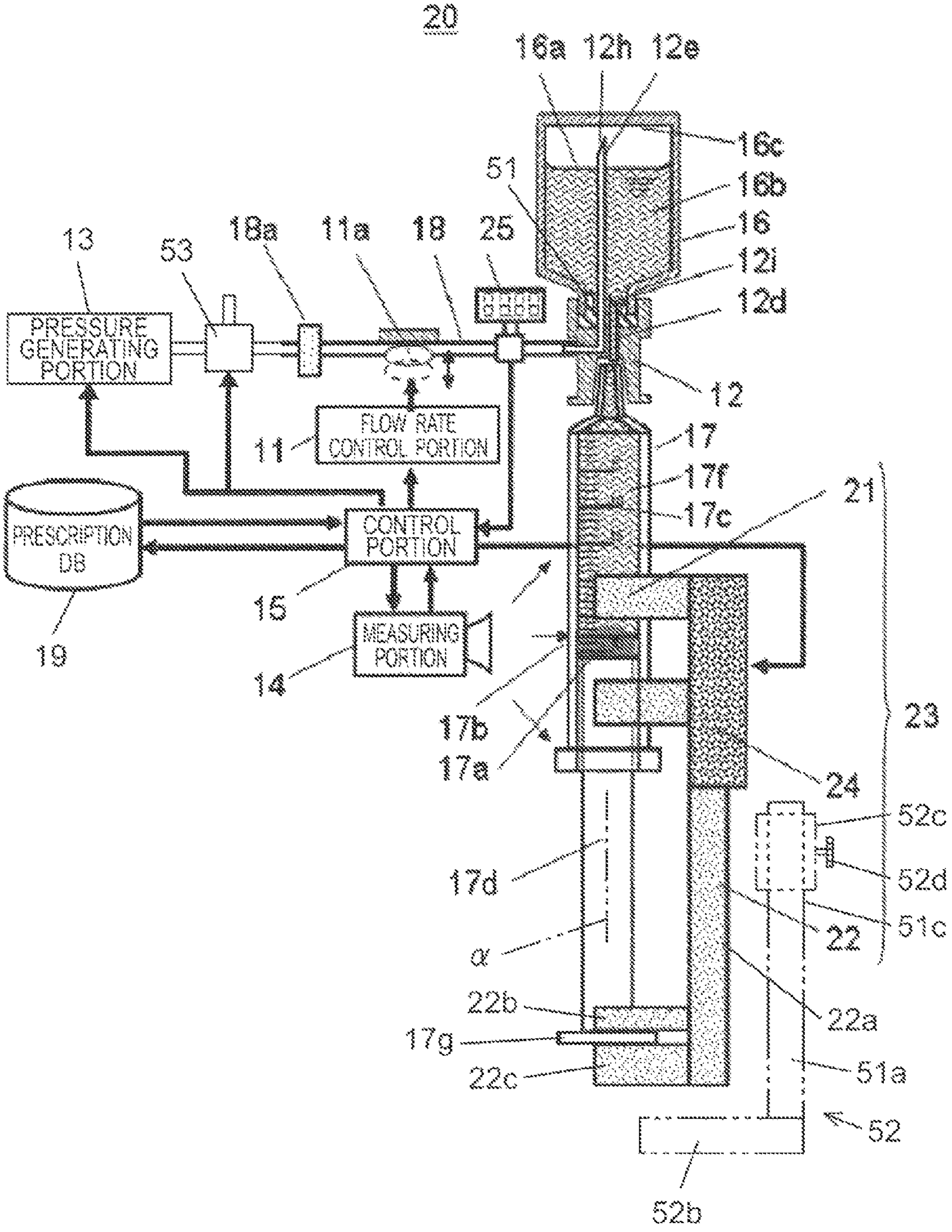
FIG. 8 is a side view schematically illustrating an overall structure of a medicinal solution injection apparatus according to an embodiment 2 of the present invention.

FIG. 8 is a side view schematically illustrating an overall structure of a medicinal solution injection apparatus 20 according to an embodiment 2 of the present invention.

Similarly to the medicinal solution injection apparatus 10 according to the embodiment 1, the medicinal solution injection apparatus 20 according to the embodiment 2 is provided with the composite needle 12 for injecting the medicinal solution, the pressure generating portion 13 configured to discharge the compressed gas, the flow rate control portion 11 configured to control the flow rate of the compressed gas, the measuring portion 14 configured to measure the filling amount and the filling speed of the medicinal solution 16*b*, and the control portion 15 configured to control the pressure generating portion 13, flow rate control portion 11, and measuring portion 14, as illustrated in FIG. 8.

The edge 12*h* of the adjustment needle 12*e* is inserted into the vial container 16 above the liquid surface 16*a* of the medicinal solution in the vial container 16 to introduce the compressed air into the vial container 16 through the edge 12*h* of the adjustment needle 12*e*. Then, the compressed air presses the liquid surface 16*a* of the medicinal solution downward so that the medicinal solution 16*b* is injected into the syringe 17 through the edge 12*i* of the injection needle 12*d* in the medicinal solution 16*b*.

The medicinal solution injection apparatus 20 according to the embodiment 2 is different to the medicinal solution injection apparatus 10 according to the embodiment 1 in that a syringe holding section 23 including a barrel holding portion 21 and a plunger holding portion 22 is provided. The barrel holding portion 21 is provided to positionally secure a barrel 17*f* of the syringe 17. The plunger holding portion 22 holds a plunger 17*d* which positionally changes the gasket 17*a* and slides with the plunger 17*d* in the direction of a central shaft α of the barrel 17*f*. The plunger holding portion 22 according to the embodiment 2 is provided with a rod-shape portion 22*a* and grip portions 22*b* and 22*c* provided on a lower-end side of the rod-shape portion 22*a* to securely nip a jaw portion 17*g* of the plunger 17*d*. The syringe holding section 23 further has a braking portion 24 which latches the rod-shape portion 22*a* to lock the sliding movement of the plunger holding portion 22. When the measuring portion 14 of the medicinal solution injection apparatus 20 detects that the syringe 17 is filled with a predefined amount of medicinal solution, the braking portion 24 locks the sliding movement of the plunger holding portion 22.

When measured that the syringe is filled with the predefined amount of medicinal solution, the braking portion 24 locks the sliding movement of the plunger holding portion 22 to thereby forcibly stop the sliding movement of the plunger 17*d*. This avoids that the medicinal solution 16*b* exceeding the predefined amount is suctioned into the syringe 17. That is, this configuration prevents the medicinal solution 16*b* from being overly injected into the syringe, so that the medicinal solution 16*b* in an exact amount can be supplied into the syringe 17.

As illustrated with a chain double-dashed line in FIG. 8, a stopper 52 may be provided in place of the braking portion 24, the stopper 52 abutting the lower-end side of the plunger holding portion 22 to lock the sliding movement. The illustrated stopper 52 has an abutting portion 52*b*, which is a portion to abut the plunger holding portion 22, on a lower end of the rod-shape portion 51*a*. A bearing portion 51*c* of the rod-shape portion 51*a* is supported by a support portion 52*c* slidably in the direction of the central shaft α of the barrel 17*f*. The stopper 52 is moved in advance to a sliding position indicating the predefined amount of the medicinal solution, and positioning screws 52*d* are manually fastened to secure the stopper 52. The stopper 52 may be configured to automatically move based on the prescription data obtained from the prescription DB 19 or may be configured to abut a rear end of the plunger 17*d* to be latched therewith.

As illustrated in FIG. 8, a pressure gauge 25 is provided in the tube 18 between the adjustment needle 12*e* and the flow rate control valve 11*a*. The pressure gauge 25 transmits a detection signal indicating a detected pressure of the gas above the liquid surface 16*a* of the medicinal solution in the vial container 16 to the control portion 15. Accordingly, when the amount of the medicinal solution injected into the syringe 17 approaches the ultimate target value, the control portion 15 controls the flow rate control portion 11 and the pressure generating portion 13 based on the detection signal of the pressure gauge 25 indicating the pressure value to prevent the excess injection of the medicinal solution 16*b*.

The medicinal solution injection apparatus 20 according to the embodiment 2 has the pressure gauge 25 in a part of the tube 18 between the flow rate control portion 11 and the adjustment needle 12*e*. The control portion 15 controls at least one of the pressure generating portion 13, flow rate control portion 11, and syringe holding section 23 based on the detection signal outputted from the pressure gauge 25 to thereby adjust the filling amount of the medicinal solution 16*b* injected into the syringe 17. According to the technical feature, the gas pressure in the vial container 16 can be directly read, and the filling amount and the injection progress of the medicinal solution 16*b* can be thereby accurately grasped.

Figure 9:
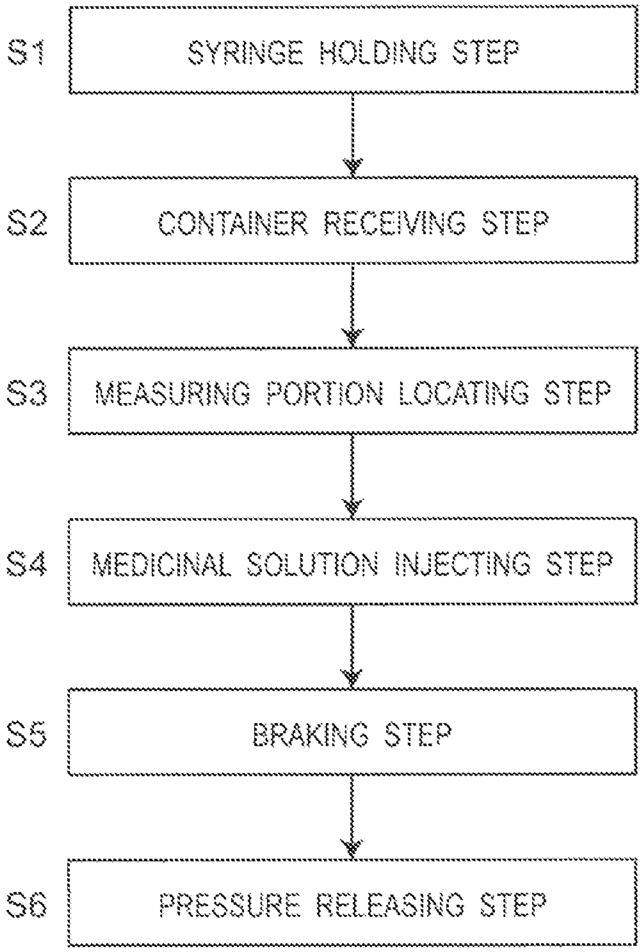
FIG. 9 is a flow chart of a medicinal solution injection method according to the embodiment 2.
Figure 10:
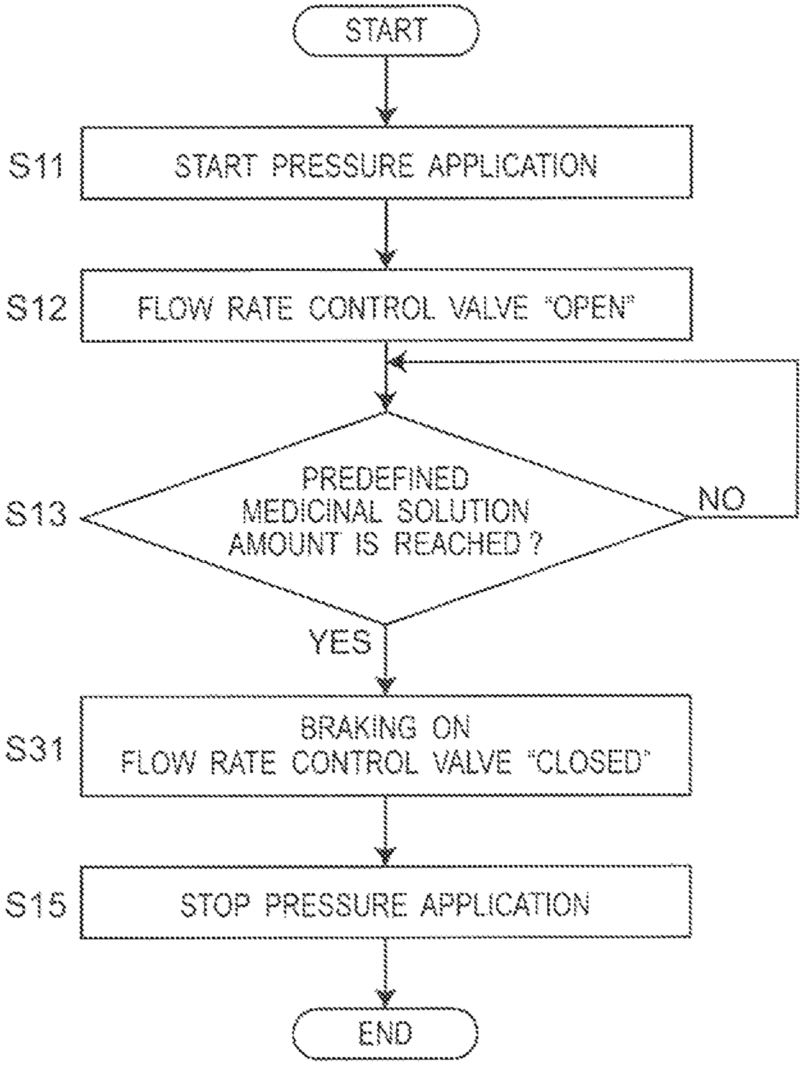
FIG. 10 is a flow chart illustrating in detail a medicinal solution injecting step of the medicinal solution injection method according to the embodiment 2.
Figure 11:
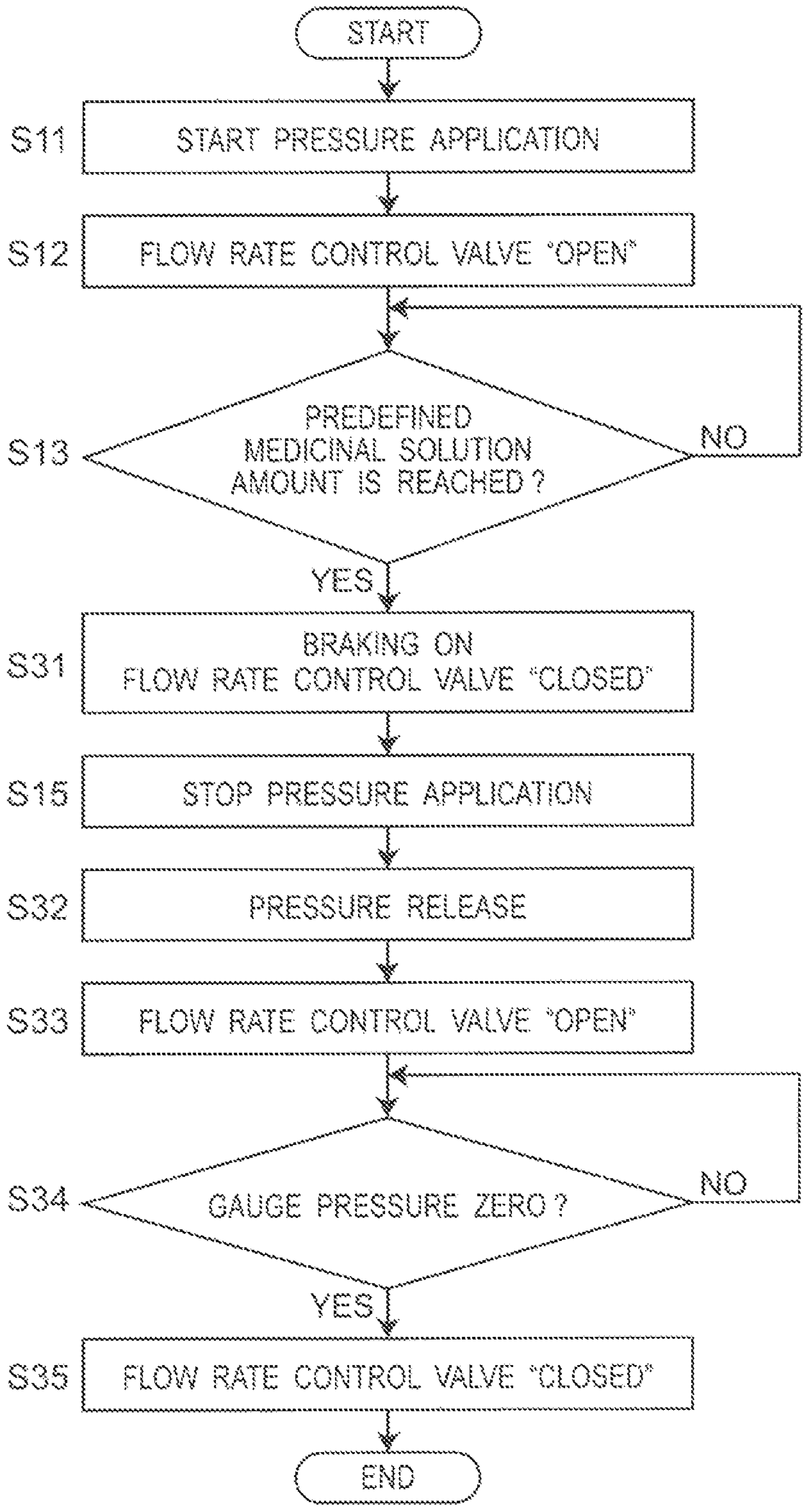
FIG. 11 is a flow chart illustrating in detail the medicinal solution injecting step of the medicinal solution injection method according to the embodiment 2.

A medicinal solution injection method using the medicinal solution injection apparatus 20 according to the embodiment 2 is hereinafter described. FIG. 9 is a flow chart of a medicinal solution injection method according to the embodiment 2. FIGS. 10 and 11 are flow charts specifically illustrating a medicinal solution injecting step (Step S4) in the medicinal solution injection method of FIG. 9 according to the embodiment 2.

As illustrated in FIG. 9, the medicinal solution injection method according to the embodiment 2 uses the medicinal solution injection apparatus 20 described so far (see FIG. 8). The medicinal solution injection method includes the syringe holding step S1, the container receiving step S2, the measuring portion locating step S3, the medicinal solution injecting step S4, and a braking step S5. Steps S1 to S4 according to the embodiment 2 are the same steps as those of the embodiment 1. The medicinal solution injection method according to the embodiment 2 is different to the medicinal solution injection method according to the embodiment 1 in that the braking step S5 is further included.

The braking step S5 is a step in which the plunger holding portion 22 is locked by the braking portion 24 when the measuring portion 14 detects that the syringe 17 is filled with the predefined amount of medicinal solution. The braking step S5, when performed in the medicinal solution injection apparatus 20 including the syringe holding section 23, can reliably prevent the medicinal solution 16*b* from being overly injected into the syringe 17.

As illustrated in FIG. 9, the medicinal solution injection method may include a pressure releasing step S6 after the medicinal solution injecting step S4. The pressure releasing step S6 is a step in which the gas pressure in the vial container 16 is reduced by the pressure generating portion 13 through the adjustment needle 12*e*, tube 18, and flow rate control valve 11*a* to be finally as low as at most atmospheric pressure. The pressure release thus performed can more reliably prevent the medicinal solution 16*b* in the vial container 16 and the syringe 17 from being exposed to atmosphere when the syringe 17 is removed from the composite needle 12. As a result, the medicinal solution injection method can be safely performed.

Figure 12:
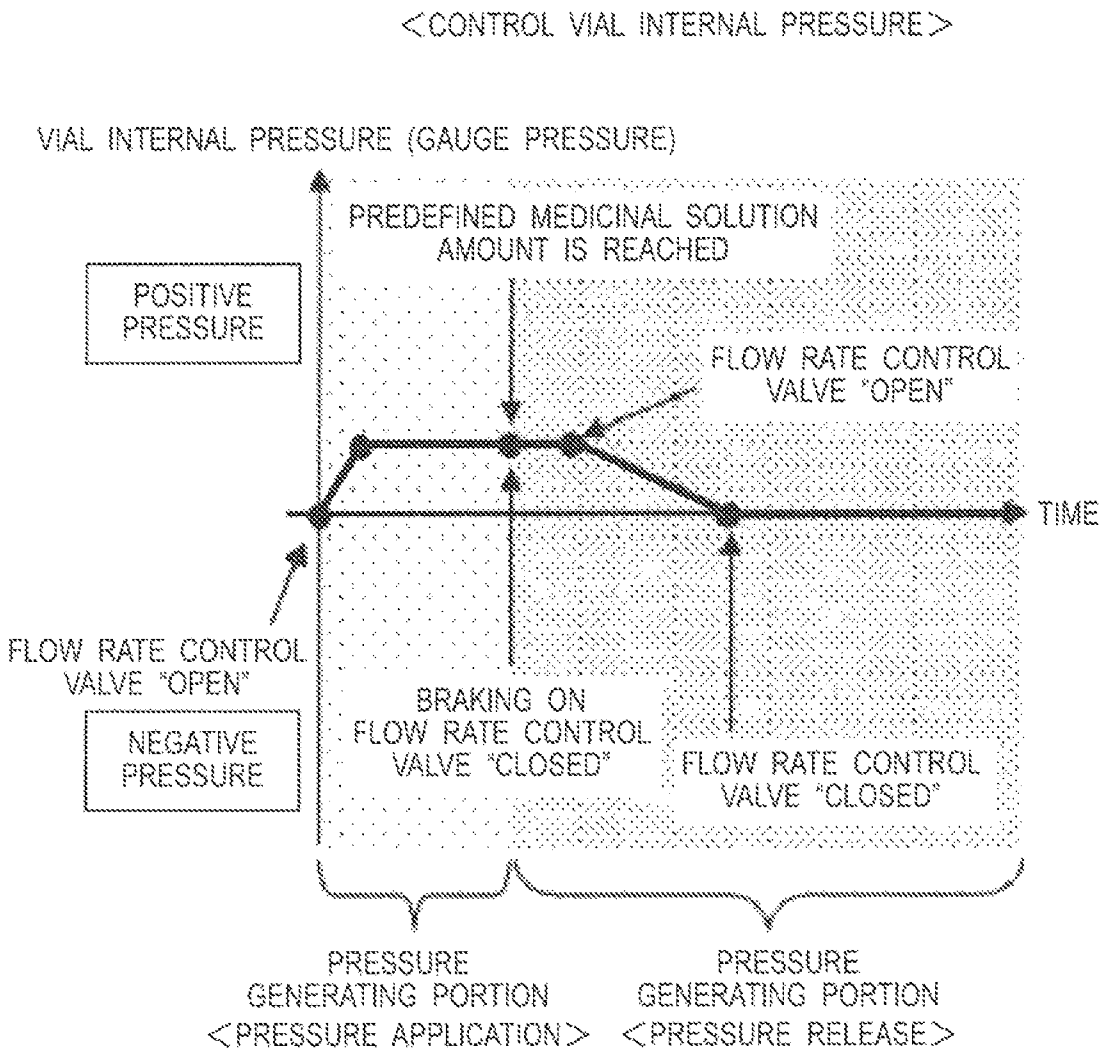
FIG. 12 is a diagram illustrating how an internal pressure of a vial in the vial container is controlled to change with time through pressure application and pressure release in a pressure releasing step according to the embodiment 2.

The flow chart for injecting the medicinal solution 16*b* using the medicinal solution injection apparatus 20 illustrated in FIG. 8 is described in more detail referring to FIGS. 10 and 11. FIG. 10 illustrates a case not including the pressure releasing step S6, whereas FIG. 11 illustrates a case including the pressure releasing step S6. FIG. 12 is a diagram illustrating how the gas pressure in the vial container 16 (hereinafter, called vial internal pressure) is controlled to change with time through pressure application and pressure release by the pressure generating portion 13 in the pressure releasing step S6.

The flow chart of medicinal solution injection illustrated in FIG. 10 is identical to the flow chart of medicinal solution injection illustrated in FIG. 3 according to the embodiment 1 except Step S31 included in place of Step S14. Any steps but Step S31, which are the same steps as those described in the embodiment 1, are not described again.

The medicinal solution 16*b* is injected into the syringe 17 until the predefined medicinal solution amount predefined in the prescription obtained from the prescription DB 19 is reached in Step S13 of FIG. 10. Then, the sliding movement of the plunger holding portion 22 is forcibly stopped by the locking of the braking portion 24 of the syringe holding section 23 (step S31). At the same time, the flow rate control valve 11*a* is "closed" to become a closed state. Accordingly, it is more reliably avoided that the medicinal solution 16*b* is overly injected into the syringe 17.

In the flow chart of FIG. 11, the compressed air is continuously discharged until the pressure application by the pressure generating portion 13 stops in Step S15 after the pressure application started (step S11). Therefore, the vial internal pressure is kept at a positive pressure. Then, the flow rate control valve 11*a* is "open" to become an opened state (step S33) since the pressure release stars (step 32). At substantially the same time, a pressure release valve 53 provided in the pressure generating portion 13, for example, releases the positive-side pressure into atmosphere. The state of pressure release of the vial internal pressure can be confirmed by checking a gauge pressure of the pressure gauge 25 (step S34). The gauge pressure reduces up to 0 as illustrated in FIG. 12. When the gauge pressure equals to 0, the flow rate control valve 11*a* is "closed" to become a closed state (step S35).

According to the method, the vial internal pressure is constantly as low as atmospheric pressure after the injection of the medicinal solution 16*b* is completed, so that the medicinal solution 16*b* in the vial container 16 and the syringe 17 can be reliably prevented from being suddenly exposed to atmosphere when the syringe 17 is removed from the composite needle 12. As a result, the medicinal solution injection method can be safely performed. The edge 12*h* of the adjustment needle 12*e* of the composite needle 12 is always located above the liquid surface 16*a* of the medicinal solution 16*b* in the vial container 16 (outside the liquid surface). This prevents possible backflow of the medicinal solution 16*b* through the adjustment needle 12*e* toward the pressure generating portion 13 during the pressure release.

Embodiment 3

Figure 13:
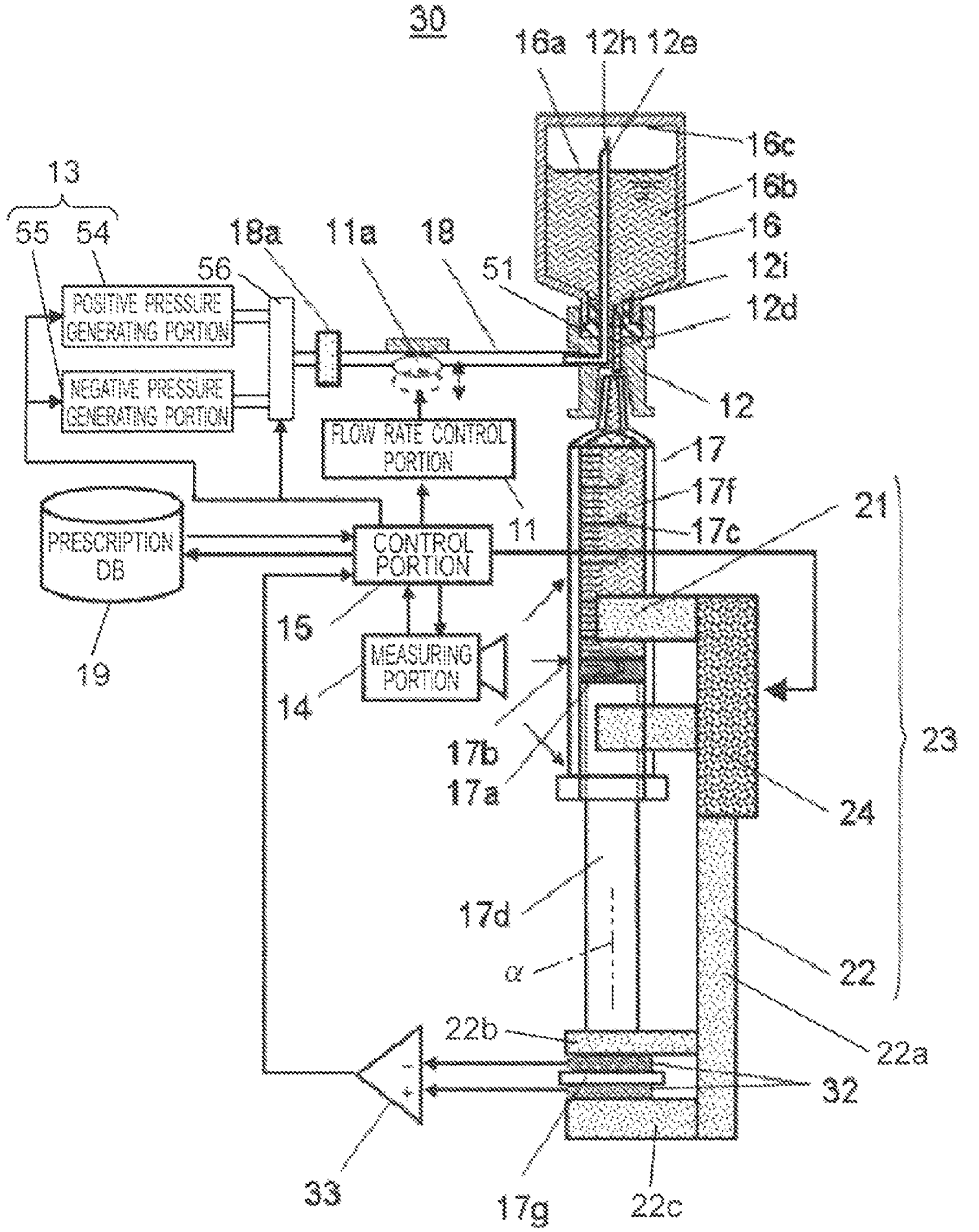
FIG. 13 is a side view schematically illustrating an overall structure of a medicinal solution injection apparatus according to an embodiment 3 of the present invention.

FIG. 13 is a side view schematically illustrating an overall structure of a medicinal solution injection apparatus 30 according to an embodiment 3 of the present invention.

Similarly to the medicinal solution injection apparatus 20 according to the embodiment 2, the medicinal solution injection apparatus 30 according to the embodiment 3 is provided with the composite needle 12 for injecting the medicinal solution, the measuring portion 14 configured to measure the filling amount and the filling speed of the medicinal solution, a pressure generating portion 13, and the control portion 15 configured to control the pressure generating portion 13, flow rate control portion 11, and measuring portion 14, as illustrated in FIG. 13. The pressure generating portion 13 of the medicinal solution injection apparatus 30 has a pressure application function for discharging the compressed air and a pressure reduction function for reducing the pressure of the compressed air to a pressure level slightly lower than atmospheric pressure. More specifically, the pressure generating portion 13 of the medicinal solution injection apparatus 30 is provided with a positive pressure generating portion 54 and a negative pressure generating portion 55. The pressure generating portion 13 is further provided with a switchover valve 56 for selecting one of the positive pressure generating portion 54 and the negative pressure generating portion 55 to connect the selected one to inside of the vial container 16 by way of the tube 18.

Similarly to the embodiment 2, the edge 12*h* of the adjustment needle 12*e* is located above the liquid surface 16*a* of the medicinal solution in the vial container 16 to introduce the compressed air into the vial container 16 through the edge 12*h* of the adjustment needle 12*e*. The compressed air thus introduced presses the liquid surface 16*a* of the medicinal solution downward so that the medicinal solution 16*b* is injected into the syringe 17 through the edge 12*i* of the injection needle 12*d* in the medicinal solution 16*b*.

The medicinal solution injection apparatus 30 according to the embodiment 3 is provided with a pair of pressure sensors 32 between the syringe holding section 23 and the jaw portion 17*g* of the plunger 17*d* in place of the pressure gauge 25 provided in the embodiment 2. Examples of the pressure sensor 32 are a capacitance type pressure sensor and a resistive pressure sensor in which a pressure sensitive rubber or a distortion gauge is used. With this configuration, when the plunger holding portion 22 is locked, signals, for example, differential signals from the pair of pressure sensors 32 are detected to determine a direction where the plunger 17*d* is drawn. The differential signals of the pressure sensors 32 are connected to a detector circuit including a differential amplifier 33 to be signal-processed. The detector circuit including the differential amplifier 33 is connected to the control portion 15.

With this configuration, whether the pressures of the plunger 17*d* and the medicinal solution 16*b* in the syringe 17 are positive or negative can be determined in real time. Further, the medicinal solution 16*b* is prevented from being overly injected into the syringe 17 so that the syringe 17 is efficiently filled with the exact amount of the medicinal solution 16*b*. Further, the gas pressure in the vial container 16 can be reduced to a negative pressure without fail before removing the syringe 17 from the composite needle 12. This surely prevents the medicinal solution 16*b* in the vial container 16 and the syringe 17 from being exposed to atmosphere, thereby safely injecting the medicinal solution 16*b* into the syringe 17.

Figure 14:
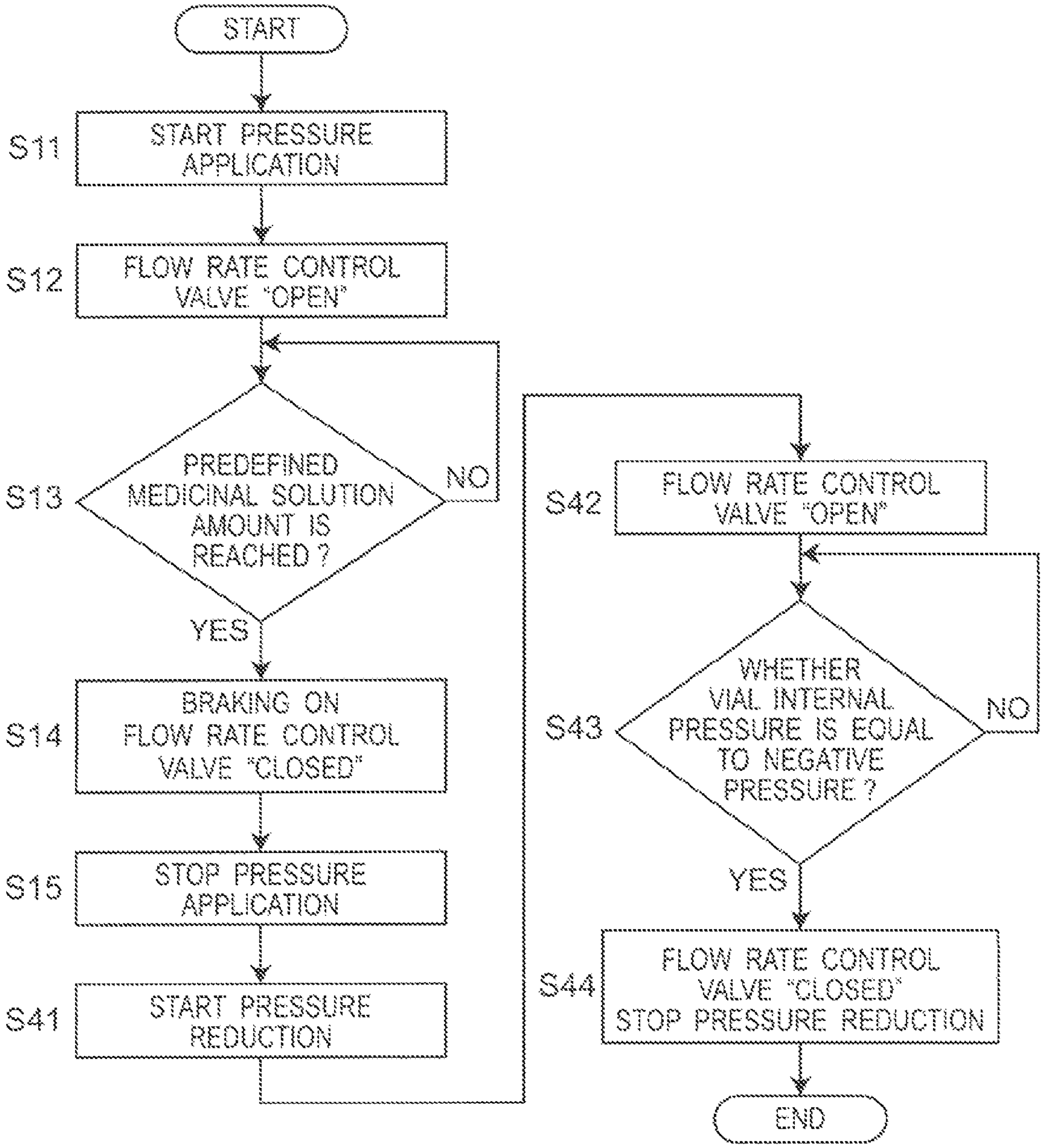
FIG. 14 is a flow chart illustrating in detail a medicinal solution injecting step of a medicinal solution injection method according to the embodiment 3.
Figure 15:
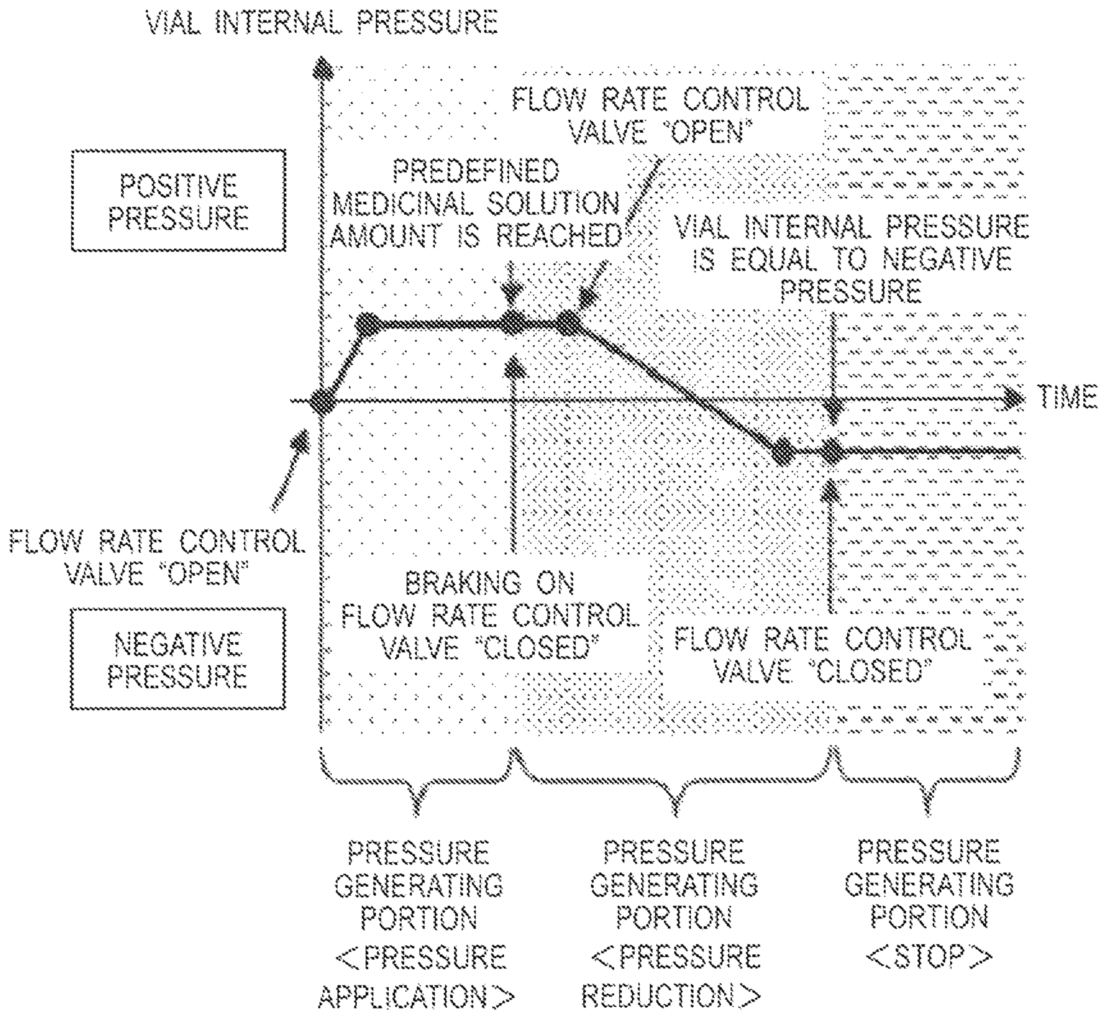
FIG. 15 is a diagram illustrating how an internal pressure of a vial in the vial container is controlled to change with time through pressure application and pressure reduction in the medicinal solution injection method according to the embodiment 3.
Figure 16:
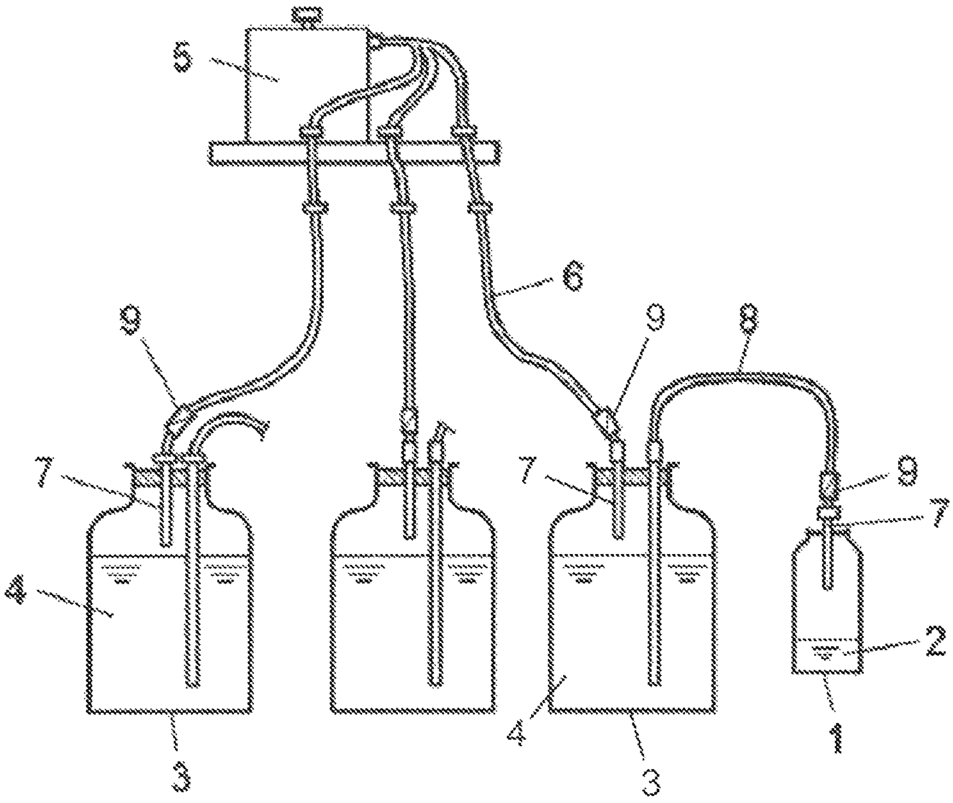
Fig.16 PRIOR ART
FIG. 16 is a structural view of a conventional medicinal solution injection apparatus.

The flow chart for injecting the medicinal solution 16*b* into the syringe 17 using the medicinal solution injection apparatus 30 illustrated in FIG. 13 is described in more detail referring to FIGS. 14 and 15.

FIG. 14 is a flow chart further including a pressure reduction process added after process in the flowchart of FIG. 10 described in the embodiment 2. FIG. 15 illustrates how the internal pressure of the vial container 16 is controlled to change with time through pressure application and pressure reduction by the pressure generating portion 13.

After the pressure application by the pressure generating portion 13 (positive pressure generating portion 54) is ceased (step S15), the gas in the vial container 16 is suctioned through the tube 18 for pressure reduction by using the pressure reduction function of the pressure generating portion 13 (step S41). More specifically, the switchover valve 56 of the pressure generating portion 13 switches the connection with the inside of the vial container 16 through the tube 18, from the positive pressure generating portion 54 to the negative pressure generating portion 55. Then, the negative pressure generating portion 55 is activated to start the suctioning. The flow rate control valve 11*a* which controls the inner diameter of the tube 18 is "open" to become an opened state (step S42). The control portion 15 monitors the detected signals generated from the pressure sensors 32 and the detector circuit, so that the internal pressure of the vial container 16 is reduced to as low as atmospheric pressure or a negative pressure slightly lower than atmospheric pressure (step S43). When the vial internal pressure is reduced to as low as atmospheric pressure or a negative pressure lower than atmospheric pressure by a given pressure value, the flow rate control valve 11*a* is closed to cease the pressure reduction by the pressure generating portion 13 (step S44).

The method can surely reduce the internal pressure of the vial container 16 to a negative pressure lower than atmospheric pressure. Therefore, the method can surely prevent the medicinal solution 16*b* in the vial container 16 and the syringe 17 from being suddenly exposed to atmosphere when the syringe 17 is removed from the composite needle 12. As a result, the medicinal solution injection method can be safely performed. Similarly to the embodiment 2, the edge 12*h* of the adjustment needle 12*e* of the composite needle 12 is always located above the liquid surface 16*a* of the medicinal solution in the vial container 16 (outside the liquid surface). This avoids possible backflow of the medicinal solution 16*b* toward the pressure generating portion 13 through the adjustment needle 12*e*.

The medicinal solution injection apparatus 30 according to the embodiment 3 may be further equipped with the pressure gauge 25 provided in the medicinal solution injection apparatus 20 according to the embodiment 2 so that the pressure is monitored by the pressure sensors 32 and the pressure gauge 25 both. Accordingly, the vial internal pressure can be more accurately monitored.

In the embodiments 1 to 3 described so far, the medicinal solution is pressed by the compressed air, however, other gases may be used in place of air. It is preferable to use an inactive gas which generates no reaction with the medicinal solution such as nitrogen or argon. The gas may be replaced with a liquid having a specific gravity smaller than that of the medicinal solution, for example, an oil or oil-based liquid. Unlike gasses, liquids are uncompressed when used. Therefore, the filling amount is better controllable when the medicinal solution is filled, allowing the medicinal solution to be more accurately injected to reach the ultimate target value. It is to be noted that when a liquid is used is to select any liquid which is not mixed with the medicinal solution.

INDUSTRIAL APPLICABILITY

The medicinal solution injection apparatus and the medicinal solution injection method provided by the present invention can accurately and efficiently inject the medicinal solution of the medicinal solution container into the syringe while suppressing the medicinal solution from foaming. When the medicinal solution injection apparatus and the medicinal solution injection method are used, medical personnel, such as pharmacists and nurses, need not perform a medicinal solution suctioning operation to a syringe which requires a careful handling for safety. As a result, such a heavy work load conventionally imposed on the medical personnel can be greatly reduced in medical facilities such as hospitals.

DESCRIPTION OF REFERENCE SYMBOLS

10, 20, 30 medicinal solution injection apparatus
11 flow rate control portion
11*a* flow rate control valve
11*b* valve driver
12 composite needle
12*a* receiving port
12*b* holding port
12*c* needle base portion
12*d* injection needle
12*e* adjustment needle
12*f* side surface
12*g* end portion
12*h*, 12*i* edge
13 pressure generating portion
14 measuring portion
15 control portion
16 vial container
16*a* liquid surface of medicinal solution
16*b* medicinal solution
16*c* bottom section
17 syringe
17*a* gasket
17*b* front-end portion
17*c* scale mark
17*d* plunger
17*f* cylinder
17*g* jaw portion
18 tube
18*a* bacteria blocking filter
19 prescription DB
21 cylinder holding section
22 plunger holding portion
22*a*, 52*a* rod-shape portion
22*b*, 22*c* grip portion
23 syringe holding section
24 braking portion
25 pressure gauge
32 pressure sensor
33 differential amplifier
51 rubber cap
52 stopper
52*b* abutting portion
52*c* support portion
52*d* positioning screw
53 pressure release valve
54 positive pressure generating portion
55 negative pressure generating portion
56 switchover valve

The invention claimed is:

1. A medicinal solution injection apparatus, comprising:

a composite needle including a receiving port for receiving a medicinal solution container, a holding port for holding a syringe, an injection needle inserted through a needle base portion to communicate the receiving port with the holding port, and an adjustment needle inserted through the needle base portion from a side surface of the needle base portion to the receiving port and located in parallel with the injection needle in the receiving port;

a fluid feeding portion configured to feed a fluid into the medicinal solution container received by the receiving port through a feed tube connected to an end portion of the adjustment needle on a side of the side surface;

a measuring portion configured to measure at least one of a filling amount and a filling speed of a medicinal solution injected into the syringe from the medicinal solution container through the injection needle based on a position of a gasket in the syringe held by the holding port; and a control portion configured to control a feeding amount of the fluid from the fluid feeding portion based on a result of the measurement by the measuring portion.

2. The medicinal solution injection apparatus as claimed in claim 1, wherein the control portion makes the fluid feeding portion feed the fluid only when an edge of the adjustment needle is located above a liquid surface of the medicinal solution contained in the medicinal solution container received by the receiving port.

3. The medicinal solution injection apparatus as claimed in claim 1, wherein the fluid feeding portion comprises a flow rate control valve for controlling a degree of opening in an inner diameter of the feed tube, and the control portion controls the degree of opening of the flow rate control valve with a given duty ratio.

4. The medicinal solution injection apparatus as claimed in claim 3, wherein the control portion always sets the degree of opening of the flow rate control valve to 1 until the filling amount of the medicinal solution in the syringe held by the holding port reaches a predefined filling amount, and the control portion periodically repeats an opening time when the degree of opening of the flow rate control valve is set to 1 and a closing time when the degree of opening is set to 0 after the filling amount exceeds the predefined filling amount, the control portion further gradually extends the closing time until the filling amount is close enough to a filling amount to be ultimately obtained.

5. The medicinal solution injection apparatus as claimed in claim 1, further comprising, when the syringe held by the holding port comprises a barrel, a gasket, and a plunger: a barrel holding portion for holding the barrel; a plunger holding portion for changing a position of the gasket while sliding with the plunger thereby held; and a braking portion for locking the sliding movement of the plunger holding portion, wherein the control portion allows the braking portion to lock the plunger holding portion when the measuring portion measures that the predefined filling amount of the medicinal solution is injected in the syringe.

6. The medicinal solution injection apparatus as claimed in claim 5, wherein a pair of pressure sensors are provided between the plunger holding portion and a jaw portion of the plunger, the control portion detects signals from the pair of pressure sensors when the plunger holding portion is locked to determine a direction where the plunger is drawn, and the control portion controls an amount of the fluid fed by the fluid feeding portion based on the determined direction.

7. The medicinal solution injection apparatus as claimed in claim 1, further comprising a bacteria blocking filter between the fluid feeding portion and the flow rate control valve.

8. The medicinal solution injection apparatus as claimed in claim 1, wherein the fluid is a gas or a liquid having a specific gravity smaller than a specific gravity of the medicinal solution.

9. A medicinal solution injection method comprising steps of:

preparing a medicinal solution injection apparatus comprising a composite needle including a needle base portion, an injection needle inserted through the needle base portion to communicate a receiving port with a holding port, and an adjustment needle inserted through the needle base portion from a side surface of the needle base portion to the receiving port and located in parallel with the injection needle in the receiving port;

holding a syringe in the holding port;

receiving a medicinal solution container in the receiving port; locating an edge of the adjustment needle above a liquid surface of a medicinal solution contained in the medicinal solution container after the injection needle and the adjustment needle are inserted in the medicinal solution container;

measuring a front-end position of a gasket of the syringe;

feeding a fluid into the medicinal solution container through an end portion of the adjustment needle on a side of the side surface using the fluid feeding portion based on the front-end position of the gasket;

and injecting the medicinal solution contained in the medicinal solution container into the syringe through the injection needle.

10. The medicinal solution injection method as claimed in claim 9, wherein the injection of the medicinal solution from the medicinal solution container into the syringe includes an intermittent open drive operation in which an opening state which connects the medicinal solution container to the fluid feeding portion, and a closing state which disconnects the medicinal solution container from the fluid feeding portion are alternately repeated; and a length of time of the closing state is gradually extended in the intermittent open drive operation.

11. The medicinal solution injection method as claimed in claim 9, wherein the medicinal solution injection apparatus further comprises a barrel holding portion for holding a barrel of the syringe, a plunger holding portion for holding a plunger configured to change a position of a gasket of the syringe while sliding with the plunger thereby held, and a braking portion for locking the sliding movement of the plunger holding portion, and the braking portion locks the plunger holding portion when the measuring portion measures that a predefined filling amount of the medicinal solution is filled in the syringe.

12. The medicinal solution injection method as claimed in claim 9, wherein after the injection of the medicinal solution into the medicinal solution container is completed, the fluid feeder reduces a pressure of the fluid in the medicinal solution container to at most atmospheric pressure through the adjustment needle, the feed tube, and the flow rate control valve.

13. The medicinal solution injection method as claimed in claim 9, wherein the fluid is a gas or a liquid having a specific gravity smaller than a specific gravity of the medicinal solution contained in the medicinal solution container.

* * * * *